(12) United States Patent
Banar

(10) Patent No.: US 11,027,075 B2
(45) Date of Patent: Jun. 8, 2021

(54) DEVICE FOR PERCUTANEOUS DELIVERY OF THERAPEUTIC AGENTS, AND A METHOD FOR ITS USE

(71) Applicant: Visage Sculpture, PLLC, Newton, MA (US)

(72) Inventor: Maria Banar, Newton, MA (US)

(*) Notice: Subject to any disclaimer, the term of this patent is extended or adjusted under 35 U.S.C. 154(b) by 370 days.

(21) Appl. No.: 15/341,079

(22) Filed: Nov. 2, 2016

(65) Prior Publication Data

US 2017/0049971 A1 Feb. 23, 2017

Related U.S. Application Data

(63) Continuation-in-part of application No. 14/341,265, filed on Jul. 25, 2014, now Pat. No. 9,694,142.

(51) Int. Cl.
*A61B 17/20* (2006.01)
*A61M 37/00* (2006.01)
*A61M 5/32* (2006.01)
*A61H 15/00* (2006.01)

(52) U.S. Cl.
CPC ....... *A61M 5/3287* (2013.01); *A61H 15/0092* (2013.01); *A61M 5/3298* (2013.01); *A61M 37/0015* (2013.01); *A61H 2015/0014* (2013.01); *A61H 2201/105* (2013.01); *A61M 2005/3289* (2013.01); *A61M 2037/0023* (2013.01); *A61M 2037/0061* (2013.01)

(58) Field of Classification Search
CPC ..... A61H 2015/0014; A61H 2201/105; A61M 2005/3289; A61M 2037/0023; A61M 2037/0061; A61M 37/0015; A61M 5/3298
See application file for complete search history.

(56) References Cited

U.S. PATENT DOCUMENTS

| 3,918,449 A | 11/1975 | Pistor |
| 6,565,532 B1 | 5/2003 | Yuzhakov et al. |
| 6,607,513 B1 * | 8/2003 | Down ............... A61M 37/0015 604/239 |
| 8,016,849 B2 | 9/2011 | Wenchell |

(Continued)

FOREIGN PATENT DOCUMENTS

| KR | 2008/0057657 A | 6/2008 |
| KR | 2008/0003473 U | 8/2008 |

(Continued)

OTHER PUBLICATIONS

Supplementary European Search Report for Application No. EP16920637, dated Apr. 5, 2020.

*Primary Examiner* — Rebecca E Eisenberg
(74) *Attorney, Agent, or Firm* — Law Office of Ilya Libenzon

(57) ABSTRACT

A device for percutaneous delivery of therapeutic agents includes a first wheel having an axis of rotation, a first axial surface rotably mounted on the head, a second axial surface, an outer surface, and a plurality of needles disposed upon the outer surface, each needle having a tip projecting away from the axis of rotation of the wheel. The device includes a second wheel having an axis of rotation, a first axial surface affixed to the second axial surface of the first wheel, a second axial surface, an outer surface, and a plurality of needles disposed upon the outer surface, each needle having a tip projecting away from the axis of rotation.

11 Claims, 17 Drawing Sheets

(56) References Cited

U.S. PATENT DOCUMENTS

| | | |
|---|---|---|
| 8,376,984 B2 | 2/2013 | James |
| 2008/0161747 A1* | 7/2008 | Lee ........................ A61N 1/328 |
| | | 604/20 |
| 2010/0121307 A1 | 5/2010 | Lockard et al. |
| 2010/0228203 A1 | 9/2010 | Quan et al. |
| 2011/0319865 A1 | 12/2011 | Buss |
| 2014/0031897 A1 | 1/2014 | Liebl |

FOREIGN PATENT DOCUMENTS

| | | |
|---|---|---|
| KR | 2008/0100569 A | 11/2008 |
| WO | 0191846 A2 | 12/2001 |
| WO | 03024518 A2 | 3/2003 |
| WO | 2008/004781 A1 | 1/2008 |

* cited by examiner

700

```
┌─────────────────────────────────────┐
│ Providing a Device Having a Body, a Wheel
│ Rotably Mounted on the Body, the Wheel
│ having an Axis of Rotation and an Outer
│ Surface, a Plurality of Needles Disposed upon
│ the Outer Surface, Each Needle Having a Tip
│ Projecting Away from the Axis of Rotation of
│ the Wheel, and a Reservoir Mounted on the
│ Body, the Reservoir Containing a Liquid, the
│ Reservoir Having an Opening Near to the
│ Wheel
│ 701
└─────────────────────────────────────┘
               ↓
┌─────────────────────────────────────┐
│ Causing the Liquid to Dispose from the
│ Opening onto the Wheel
│ 702
└─────────────────────────────────────┘
               ↓
┌─────────────────────────────────────┐
│ Rolling the Wheel Firmly against Skin of a
│ Patient, Causing the Needles to Puncture the
│ Skin and Deliver the Fluid into the Punctures
│ 703
└─────────────────────────────────────┘
```

*FIG. 7*

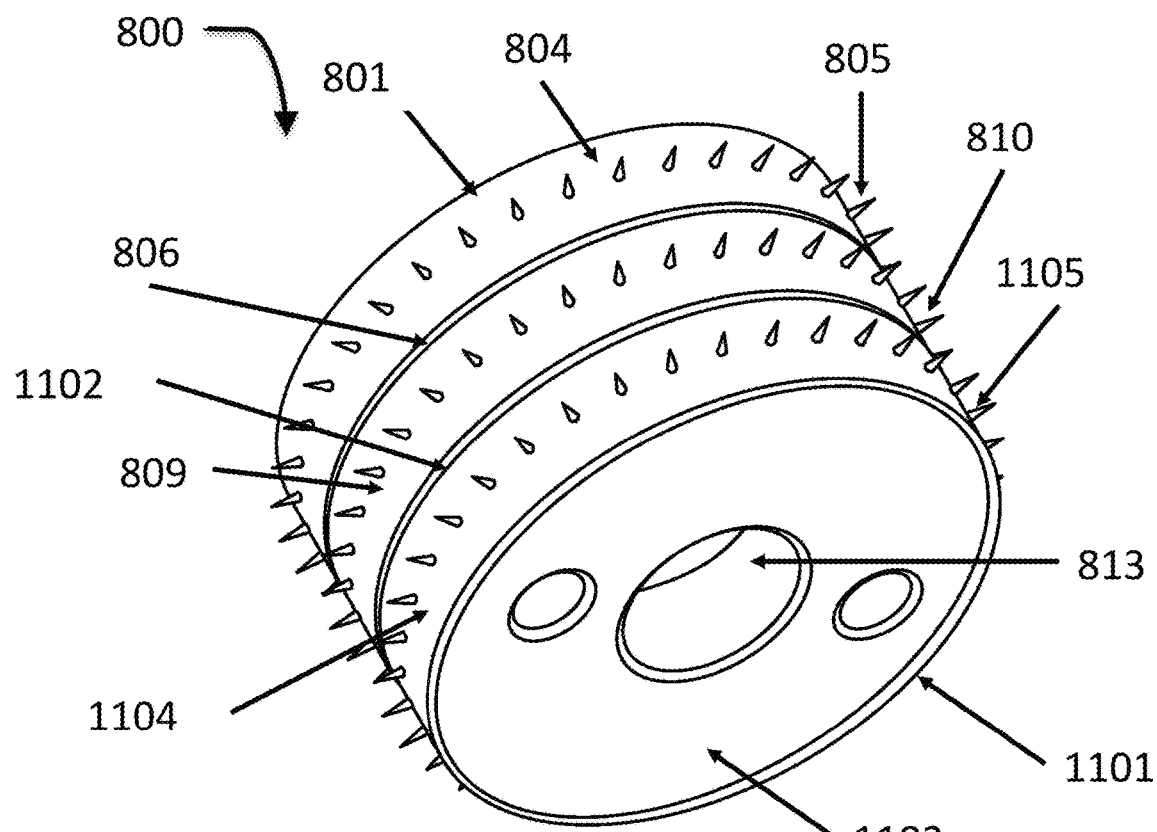
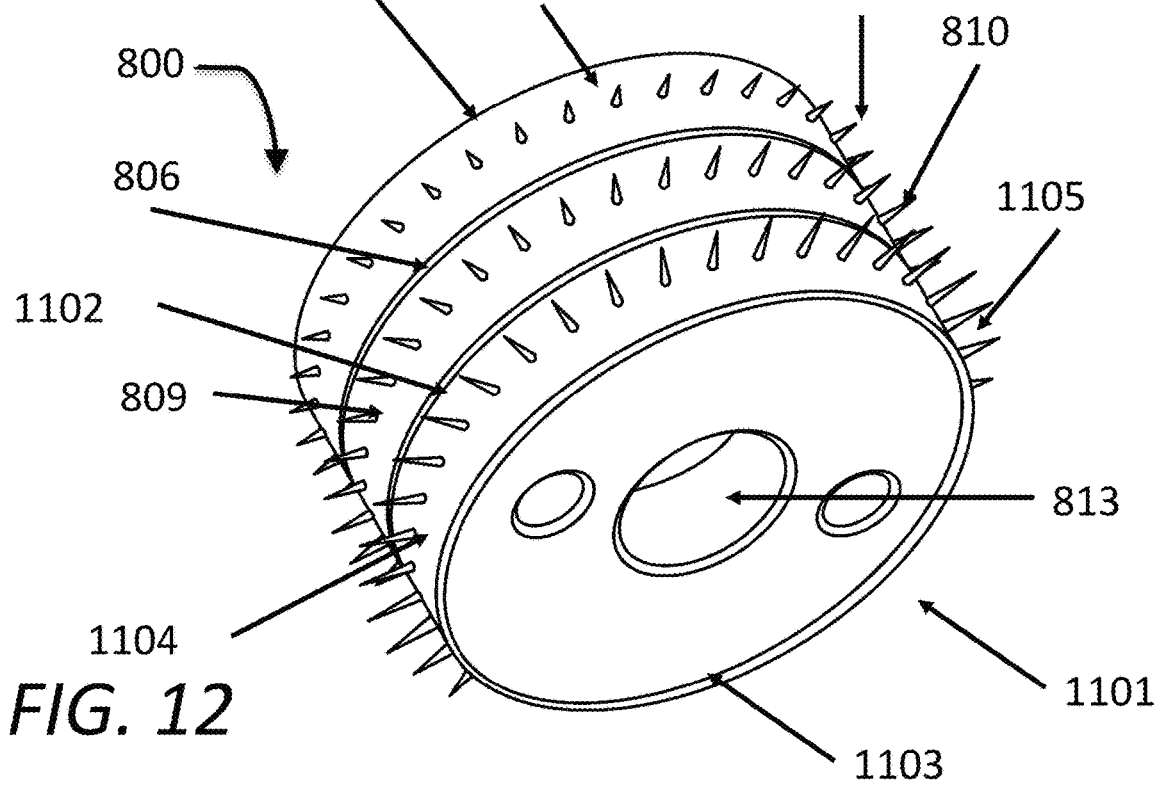

DEVICE FOR PERCUTANEOUS DELIVERY OF THERAPEUTIC AGENTS, AND A METHOD FOR ITS USE

TECHNICAL FIELD

Embodiments disclosed herein relate generally to devices for delivery of therapeutic agents into the body, and in particular to devices for percutaneous delivery of therapeutic agents.

BACKGROUND ART

A number of medical procedures that have recently become more prevalent involve delivering one or more therapeutic agents into the dermis of a user. As distinguished from subcutaneous delivery, which involves injection of agents, such as drugs, beneath the skin, percutaneous delivery requires delivery of agents into or between skin layers. Therapy that uses percutaneous agents is sometimes referred to as mesotherapy (from Greek mesos, "middle" therapeia, "to treat medically"). One therapy using percutaneous delivery that has enjoyed success in recent studies is the stimulation of dermal collagen to alleviate the effects of aging or help make scar tissue more flexible and less disfiguring. Mesotherapy to stimulate collagen production has two components: the use of carefully calibrated physical damage to stimulate collagen production via the healing process, and the delivery of chemical agents into the skin to enhance the stimulatory effect.

The first component of the therapy, known as "Microneedling," is based on the universal concept of healing of skin: when mechanical trauma occurs, skin heals by forming collagen in three stages. The first stage is inflammation. Immediately after trauma, clotting cascade is activated. Platelets secrete inflammatory agents such as cytokines and growth factors that signal fibroblasts in the dermis to produce collagen. The second stage is collagen production. Around the third week following the trauma, collagen production begins. It continues for about 2 weeks and peaks around 6th week after trauma. The third and final stage is collagen remodeling. Collagen is remodeled for the next several months. Results achieved after healing can last for several years.

Chemical agents can both assist and complement the microneedling process. Some agents may contribute by providing local nutrients to tissues during the healing process. Other agents may themselves have a further stimulatory effect. In any case, there are multiple studies proving the collagen-stimulating effect of transdermal Vitamins A, C, and E, among other agents. The process of microneedling also provides a convenient way to deliver the chemical agents into the skin of a user. Typically, the desired chemical agent or agents are placed on the surface of the patent's skin and then pushed into the skin by the needles during the microneedling process.

Delivery of therapeutic agents by microneedling is expanding to cover an ever-widening array of treatments in which a diffuse and painless delivery of an agent is preferred. However, the search continues for the most convenient approach for personal home use of these techniques. One approach is to use a dermaroller (or medical needling) in conjunction with creams or serums with vitamins. None of these methods combine the application of the therapeutic agent with the roller in a compact and convenient way suitable for home use.

Therefore, there is a need for a device that combines mechanical and chemical collagen stimulation and makes the process easier for the user.

SUMMARY OF THE EMBODIMENTS

In one aspect, a device for percutaneous delivery of therapeutic agents includes a first wheel having an axis of rotation, a first axial surface rotably mounted on the head, a second axial surface, an outer surface, and a plurality of needles disposed upon the outer surface, each needle having a tip projecting away from the axis of rotation of the wheel. The device includes a second wheel having an axis of rotation, a first axial surface affixed to the second axial surface of the first wheel, a second axial surface, an outer surface, and a plurality of needles disposed upon the outer surface, each needle having a tip projecting away from the axis of rotation.

In a related embodiment, the first axial surface of the second wheel has at least one mortise, and the second axial surface of the first wheel has at least one tenon fitting in the at least one mortise. In an additional embodiment, each of the plurality of needles mounted on the outer surface of the first wheel has a first length and each of the plurality of needles mounted on the outer surface of the second wheel has a second length, the second length differing from the first length.

Another embodiment includes a third wheel having an axis of rotation, a first axial surface affixed to the second axial surface of the second wheel, a second axial surface, an outer surface, and a plurality of needles disposed upon the outer surface, each needle having a tip projecting away from the axis of rotation. In another embodiment, each of the plurality of needles mounted on the outer surface of the first wheel has a first length, each of the plurality of needles mounted on the outer surface of the second wheel has a second length, and each of the plurality of needles mounted on the outer surface of the third wheel has a third length. In a further embodiment, the first length differs from the second length. In an additional embodiment, the first length differs from the third length. In still another embodiment, the second length differs from the third length. Another embodiment also includes a head, and the second axial surface of the third wheel is rotably mounted on the head.

Another embodiment of the device includes a head on which the first wheel and second wheel are rotably mounted. In one embodiment, the first axial surface of the first wheel is rotably mounted on the head. In another embodiment, the second axial surface of the second wheel is rotably mounted on the head. A further embodiment also includes a reservoir mounted on the head, the reservoir containing a fluid, the reservoir having an opening near to the wheel such that the fluid is disposed on the wheel through the opening.

In another aspect, a method for manufacturing a device for percutaneous delivery of therapeutic agents includes forming a first wheel having an axis of rotation, a first axial surface, a second axial surface, an outer surface, and a plurality of needles disposed upon the outer surface, each needle having a tip projecting away from the axis of rotation of the wheel, forming a second wheel having a first axial surface, a second axial surface, an outer surface, and a plurality of needles disposed upon the outer surface, each needle having a tip projecting away from the axis of rotation, and affixing the first axial surface of the second wheel to the second axial surface of the first wheel.

A related embodiment, where the first axial surface of the second wheel has at least one mortise, the second axial surface of the first wheel has at least one tenon, affixing the first axial surface of the second wheel to the second axial surface of the first wheel further involves snapping the at least one tenon into the at least one mortise.

Other aspects, embodiments and features of the device and method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The preceding summary, as well as the following detailed description of the disclosed system and method, will be better understood when read in conjunction with the attached drawings. It should be understood, however, that neither the device nor the method is limited to the precise arrangements and instrumentalities shown.

FIG. 7 is a flow chart illustrating one embodiment of the disclosed method;

FIG. 11 is a schematic diagram of an embodiment of the device;

FIG. 12 is a schematic diagram of an embodiment of the device;

DETAILED DESCRIPTION OF SPECIFIC EMBODIMENTS

Figures 1A, 1B:
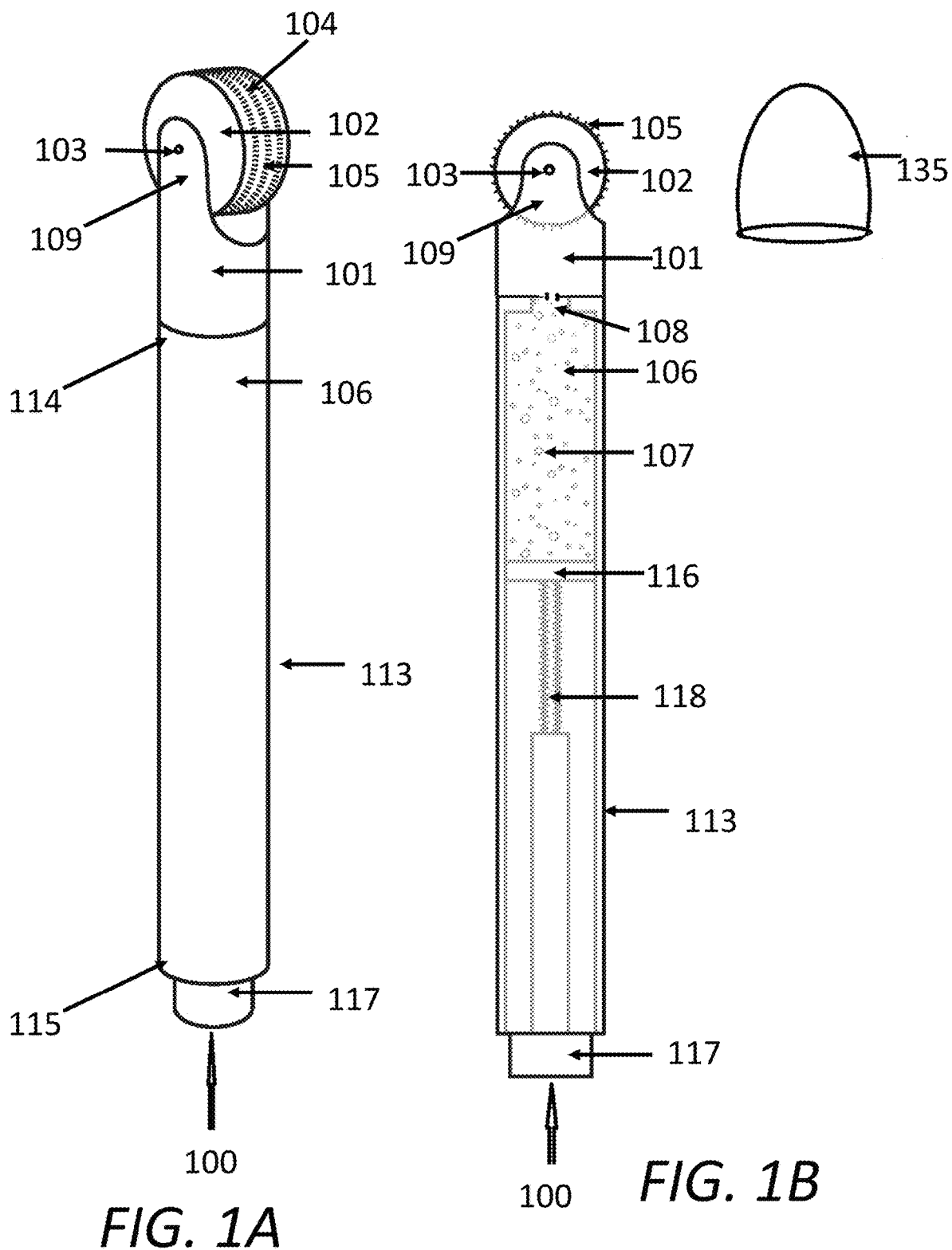
FIG. 1A is a perspective view of a disclosed device embodying the invention.
FIG. 1B is a side view, partially in section, showing an interior chamber of the disclosed device of FIG. 1A.

Embodiments of the disclosed device allow a person to deliver agents percutaneously through microneedle punctures with a single device that may be held and operated with one hand. The disclosed device may also conserve therapeutic agents and avoid messes by delivering the therapeutic agents onto the needles without first applying them to the skin of the user. As a result, the use of embodiments of the disclosed device may be more cost-effective. In some embodiments, placing the fluid directly onto the needles rather than deploying it first on the skin ensures a regular, even coat per needle, creating more predictable results. By not deploying onto the skin, enclosed embodiments avoid difficulties of application that occur when less viscous fluids flow away from the treatment area, or when volatile fluids evaporate. The disclosed embodiments also can administer more viscous fluids than designs involving hollow needles.

FIGS. 1A-6 depict embodiments of a device 100 for percutaneous delivery of therapeutic agents. As a brief overview, the device 100 includes a head 101, a wheel 102 rotably mounted on the head 101, the wheel 102 having an axis of rotation 103 and an outer surface 104. A plurality of needles is 105 disposed upon the outer surface 104, each needle having a tip projecting away from the axis of rotation 103 of the wheel 102. The device 100 may further include a reservoir 106 mounted on the head 101. The reservoir 106 may contain a fluid 107. The reservoir 106 may have an opening 108 near to the wheel 102 such that the fluid 107 is disposed on the wheel 102 through the opening 108.

Figure 2:
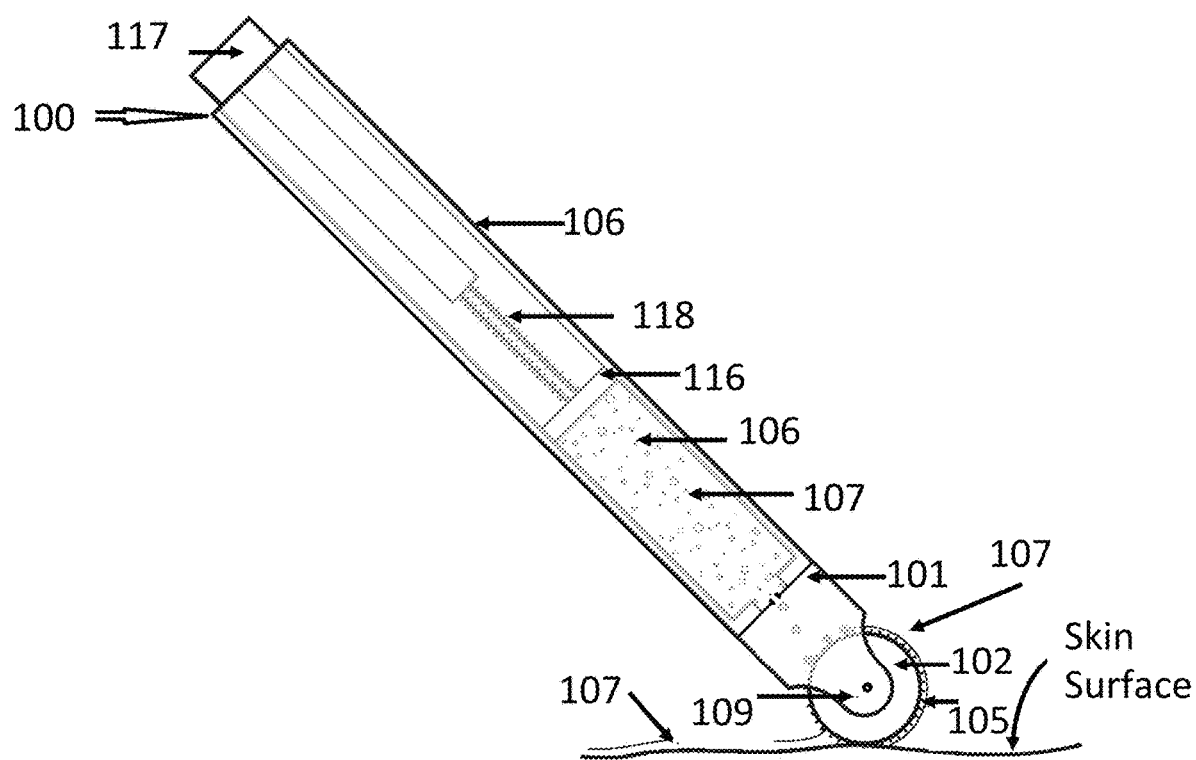
FIG. 2 is a perspective view showing operation of the disclosed device of FIG. 1.

Referring to FIGS. 1A-2 in more detail, the device 100 includes a head 101. The head 101 may be composed of any rigid material or combination of materials that will not react with the therapeutic agents. The head 101 may be composed at least in part of rigid polymers. The head 101 may be composed at least in part of rigid plastic. The head 101 may be composed at least in part of resin. The head 101 may be composed at least in part of wood. The head 101 may be composed at least in part of glass. In some embodiments, the head 101 is composed at least in part of a ceramic material. The head 101 may also be composed at least in part of metal. In some embodiments, the head 101 is composed at least in part of a composite fibrous material such as fiberglass. In some embodiments, the head 101 is hollow; for instance, the head 101 may have a hollow portion that provides a conduit for the fluid 107 to pass from the opening 108 to the wheel 102 as set forth in more detail below. The head 101 may be substantially cylindrical.

Figure 3A:
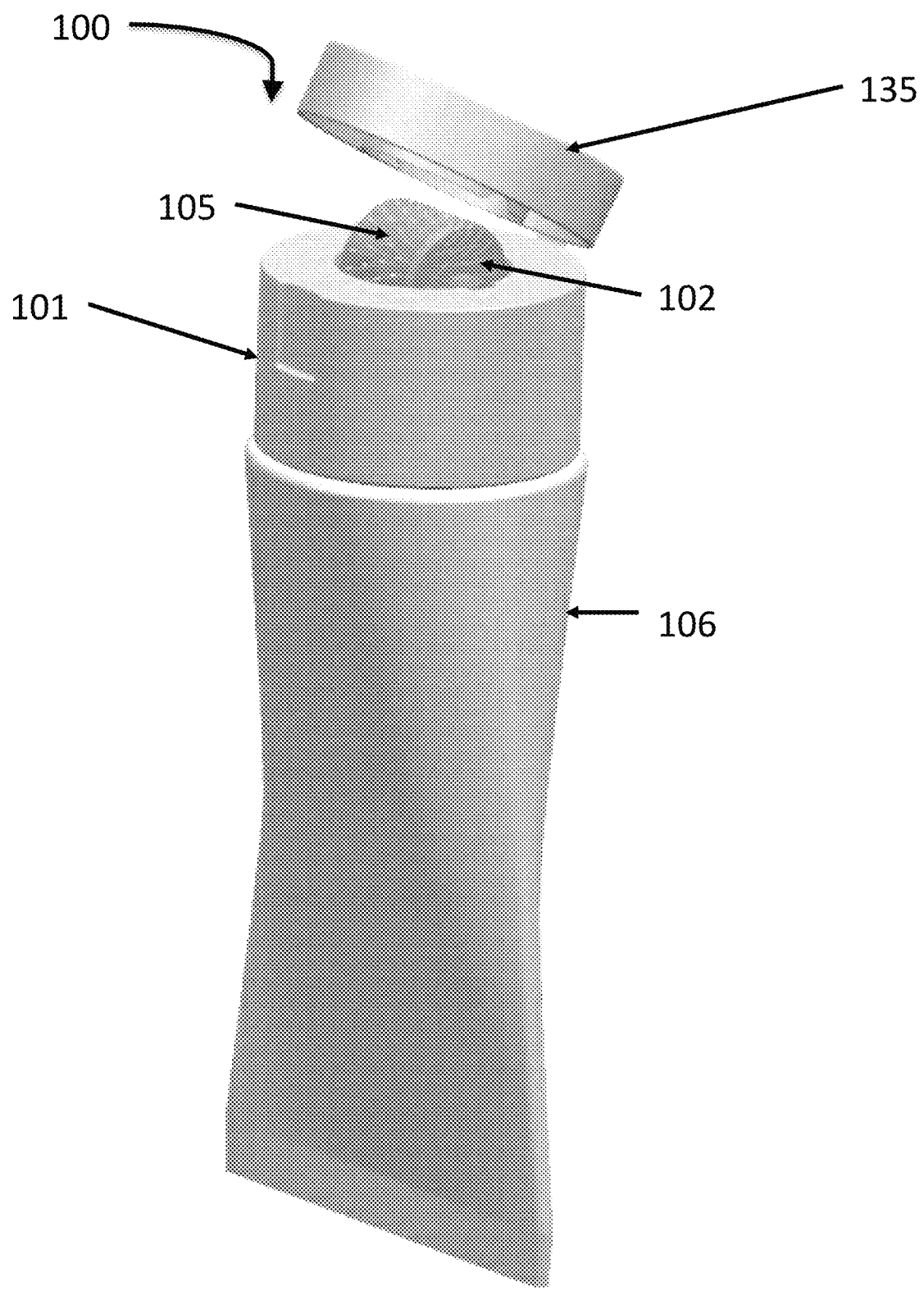
FIG. 3A is a perspective view showing another embodiment of the disclosed device.
Figure 3B:
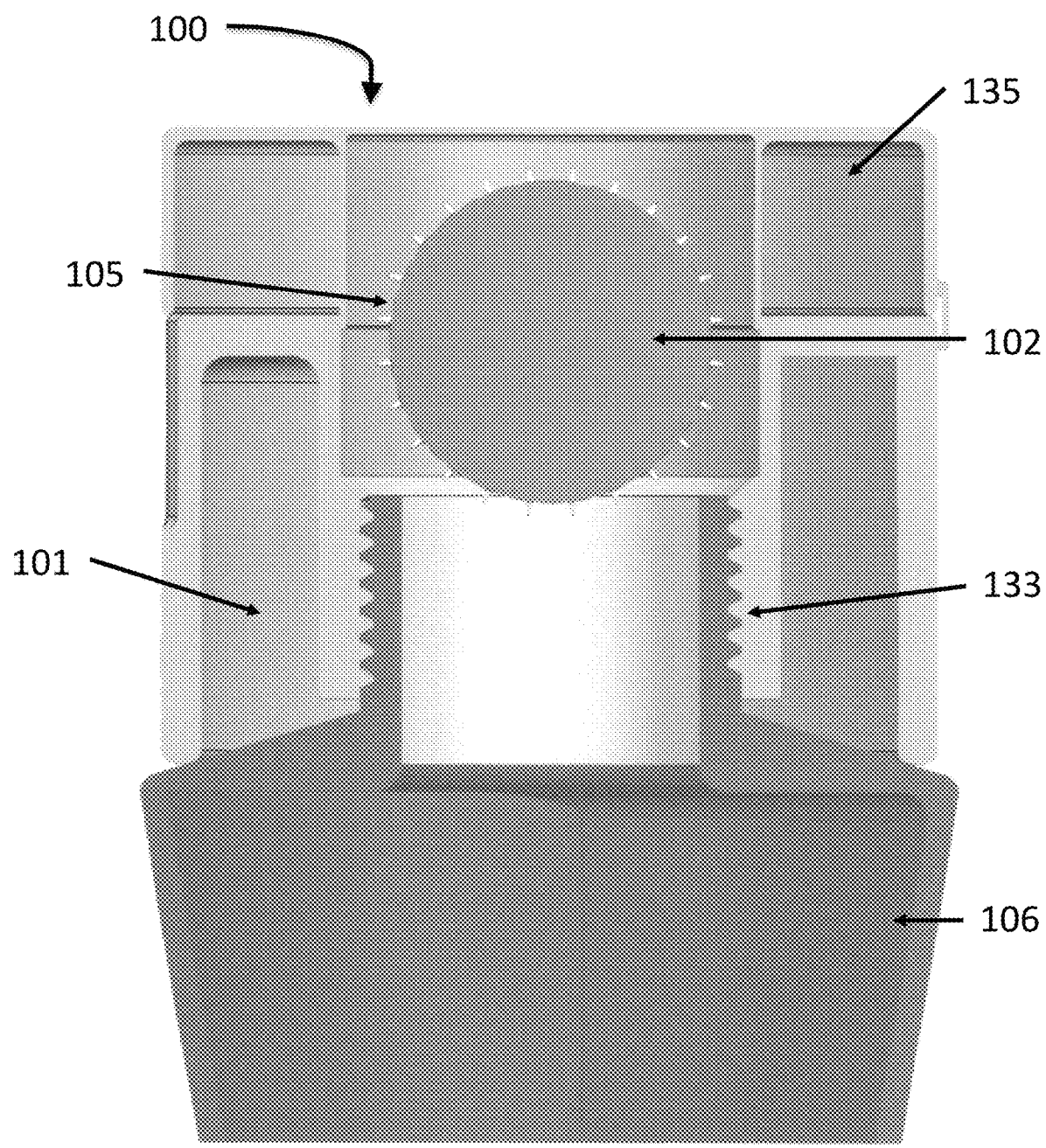
FIG. 3B is a side view, partially in section, of a portion of the embodiment of the device disclosed in FIG. 3A.
Figure 4A:
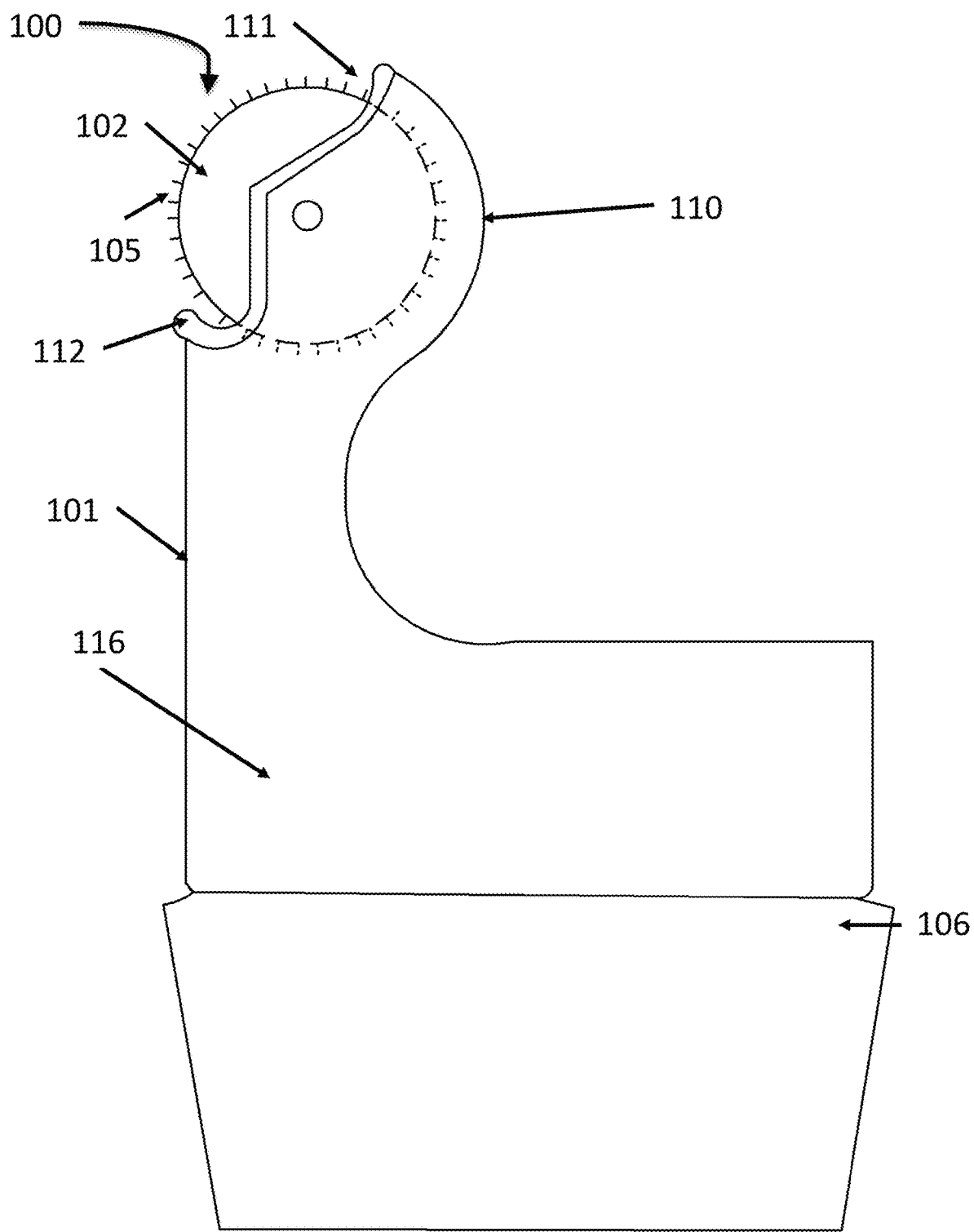
FIG. 4A is a side view, of a portion of another embodiment of the device.
Figure 4B:
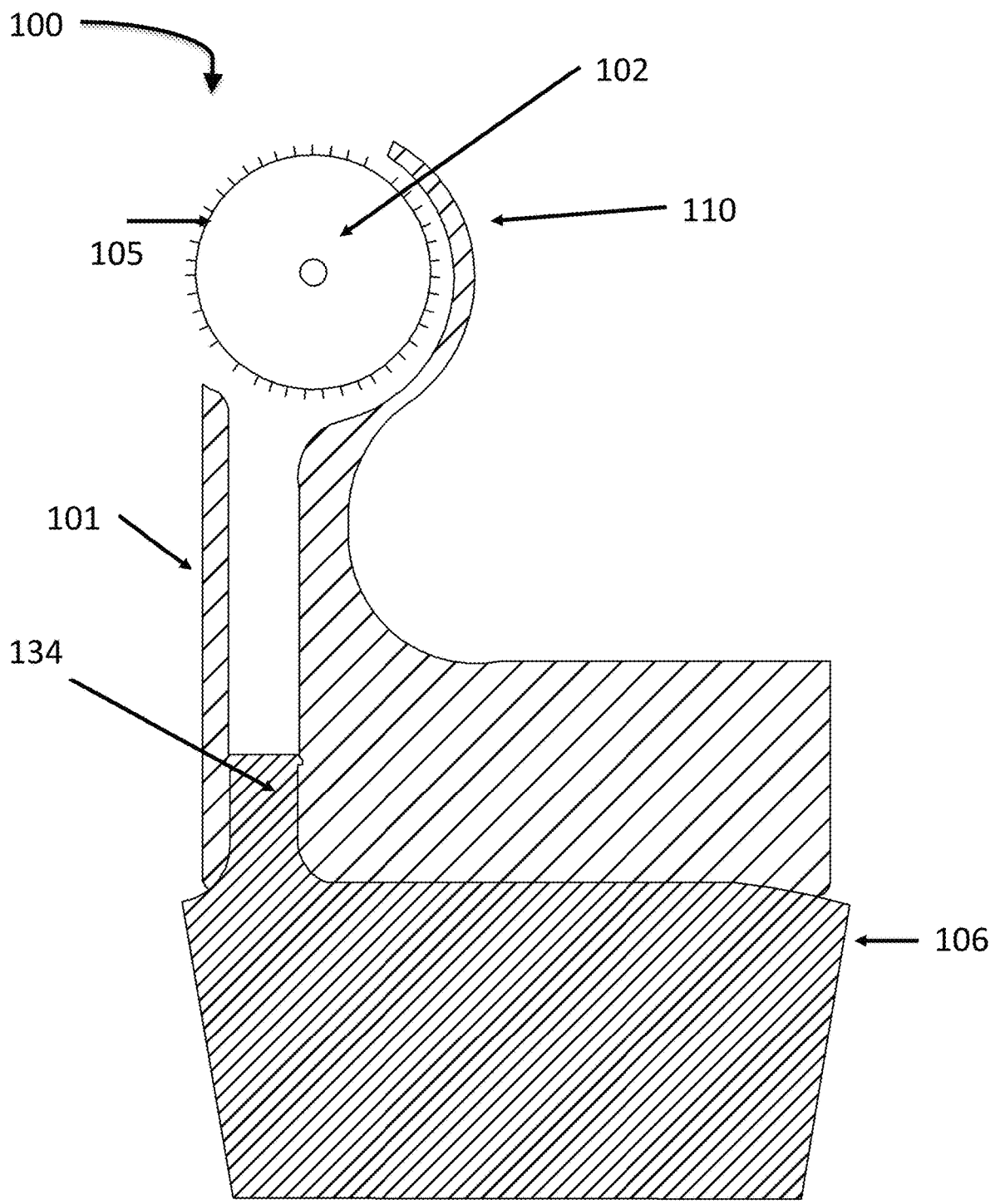
FIG. 4B is a side view, in section, of the portion of the embodiment depicted in FIG. 4A.

In some embodiments, the head 101 is detachable from the reservoir 106. The head 101 may be detachable from the reservoir 106 if the head can be detached and reattached multiple times without damage to the head 101 or reservoir 106. In some embodiments, as shown in FIG. 3B, the head is attached to the reservoir via reciprocal threading 133. In other embodiments, the reservoir 106 has an extension 134 that snaps into a hollow portion of the head 101 as shown in FIG. 4B. The device 100 may include at least one additional head 101 that may be attached to the reservoir instead of the head 101; for instance, the first head 101 may have needles a quarter of a millimeter (0.001 inches) in length for puncturing thin skin, while a second head 101 may have needles a millimeter (0.039 inches) in length for penetrating thicker skin or scar tissue. Some embodiments of the device also include a removable cap 135 that attaches to the head and covers the wheel.

Figure 5A:
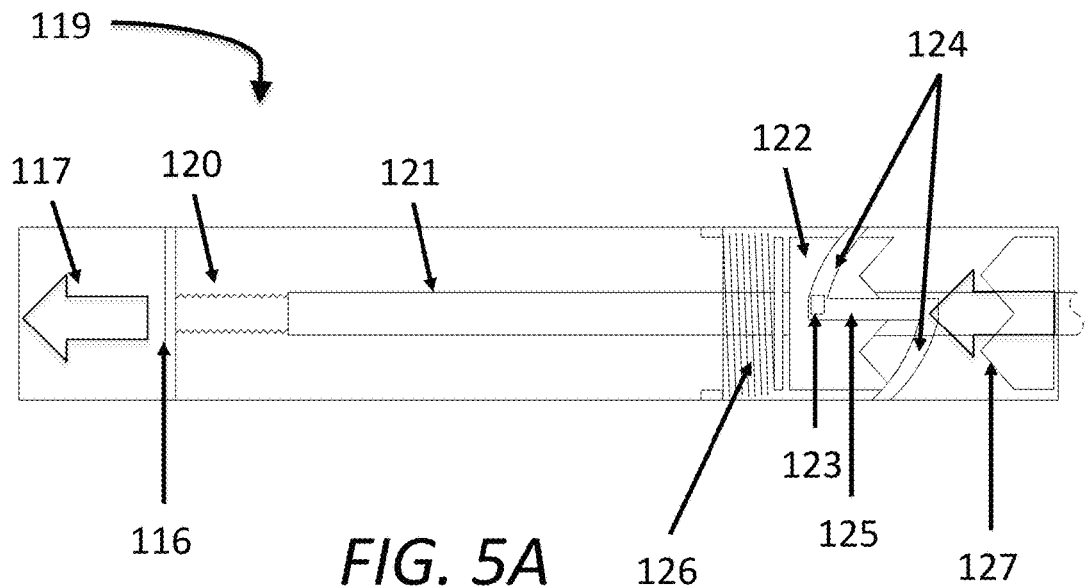
FIG. 5A is a view of an embodiment of a mechanism for advancing a plunger in embodiments of the disclosed device.
Figure 5B:
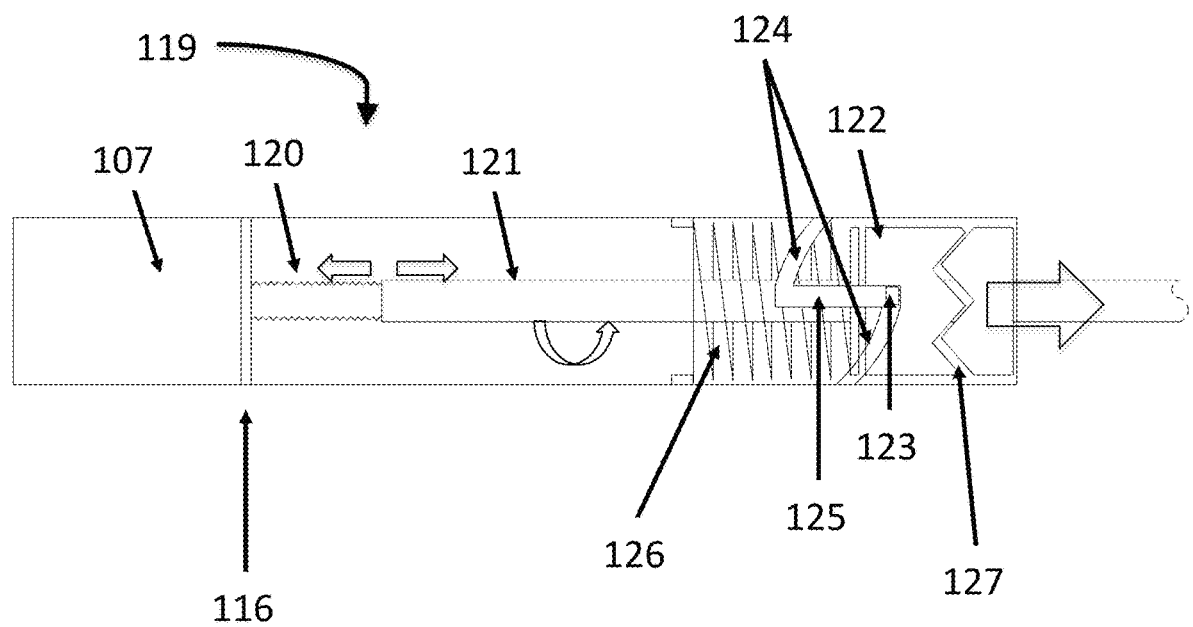
FIG. 5B is view of an embodiment of a mechanism for advancing a plunger in embodiments of the disclosed device.

In some embodiments, as shown in FIGS. 5A-B, the head 101 has a hood 110. The hood 110 may be composed of any materials suitable for the composition of the head 101. The hood 110 may be composed of the same material as the head. The hood 110 may be composed of a different material from the head. The hood 110 may be permanently attached to the head; for instance, the hood 110 may be fused to the head 101. The hood 110 may be adhered to the head. The hood 110 and the head 101 may form a single monolithic part. In some embodiments, the hood 110 is so formed that its aperture 111 contacts the skin around substantially all of its rim 112. The rim 112 of the aperture 111 may be formed of a material that is soft, such as a soft rubber or silicone, to avoid irritating the skin. The rim 112 may be formed of a material that is slick, to enable it to move against the surface of the skin without causing irritation by friction or by pulling on skin hairs. In some embodiments, the hood 110 enables a user who fears or dislikes needles to use the device 100 without having to see the needles; as described below, a cap 135 may engage against the hood such that the user may remove the cap and use the device without ever seeing the needles. As a result, the device 100 may be more generally suitable for home use. The conduit by means of which the fluid 107 passes through the head 101 may open into the hood.

The device 100 may include a wheel 102 rotably mounted on the head 101, the wheel 102 having an axis of rotation 103 and an outer surface 104. The wheel 102 may be composed of any material or combination of materials suitable for the composition of the head 101, as set forth above in reference to FIGS. 1A-2. The wheel 102 may be journaled on any suitable bearing that allows it to rotate freely about its axis of rotation 103. The wheel 102 may be mounted on an axle. The wheel 102 may be mounted by means of axle protrusions from its sides that are inserted in pits or holes in the head 101. In some embodiments, the head has a pair of members 109 that extend from the head 101 to bear the wheel 102 between the members 109. In other embodiments, the wheel 102 is disposed within the hollow portion of the head 101, as shown in FIG. 3A. In some embodiments, the wheel 102 is substantially cylindrical, the axis of rotation 103 is located at the axis of the substantially cylindrical wheel, and the outer surface 104 is the outer curved surface of the substantially cylindrical wheel. The wheel 102 may be detachable from the head 101. For instance, the head 101 may have bearings for the axle of the wheel that are open on one side, so that the axle can snap into the bearings. The members 109 may be sufficiently flexible to bend apart to allow the axle of the wheel to be inserted into a hole in each member 109; the members may be sufficiently rigid to hold the wheel in place once inserted. In some embodiments, the device 100 includes at least one additional wheel that may be attached to the head instead of the wheel. The at least one additional wheel has needles that are a different length from the needles on the wheel 102; for instance, the wheel 102 may have needles a quarter of a millimeter (0.001 inches) in length for puncturing thin skin, while an additional wheel may have needles a millimeter (0.039 inches) in length for penetrating thicker skin or scar tissue.

Some embodiments of the device 100 include a plurality of needles 105 disposed upon the outer surface 104, each needle having a tip projecting away from the axis of rotation 103 of the wheel 102. In some embodiments, the needles 105 are composed at least in part of metal; the metal may be steel. The metal may be titanium. In other embodiments, the needles are composed at least in part of a polymer. The polymer may be a silk derivative such as silk fibroin. The polymer may be silicone. The polymer may be hyaluronic acid. The polymer may be poly-L-lactic acid (PLLA). The polymer may be polylacticoglycolic acid. The polymer may be polylactic acid. The polymer may be polyglycolic acid. The polymer may be polycarbonate. The polymer may be polystyrene. The polymer may be chitosan. The needles may be composed at least in part of a carbohydrate. The carbohydrate may be cellulose. The carbohydrate may be a sugar. The needles may be made of solid or biodegradable polymers that slowly discharge molecules into the skin upon application on the needles. In some embodiments, the needles contain an additional therapeutic substance that diffuses from the needles upon insertion into the skin; for instance, the needles may contain an antibiotic or antiseptic substance to help prevent local infection. The polymer may be insoluble in the skin. In other embodiments, the needles 105 are formed from a substance that dissolves when inserted into the skin of a user; the needles may contain therapeutic agents that are released into the user's tissues when the needles dissolve. The dissolvable substance may include maltose. The dissolvable substance may include carboxymethylcellulose. The dissolvable substance may include amylopectin. The dissolvable substance may include polymethylvinylether. The dissolvable substance may include polymaleic anhydride. The dissolvable substance may include sodium hyaluronate. The dissolvable substance may include chondroitin sulphate. The dissolvable substance may include chondroitin dextrin. The dissolvable substance may include sodium alginate. The dissolvable substance may include hydroxypropyl cellulose. In some embodiments, the needles are designed to break off in the skin and continue a slow release of therapeutic agents. The needles may be formed of any combination of the above materials. For instance, the needles may be made of metal but then coated with polymers. The wheel and needles may be made of metal but then coated with polymers. The needles may be formed separately from the wheel and then attached. The needles may formed by processing the surface of the wheel; for instance, the needles may be formed by cutting, raising, or otherwise modifying portions of the surface of the wheel.

Where the wheel 102 is substantially cylindrical, each of the plurality of needles 105 may extend from the outer surface 104 of the wheel 102 along a radial line through the axis of rotation 103. Each needle may be perpendicular to the surface of the wheel 104 where the needle joins the surface. In some embodiments, each of the plurality of needles extends from the outer surface by a length of between one quarter of a millimeter (0.001 inches) and one millimeter (0.039 inches). In additional embodiments, each of the plurality of wheels has a diameter of between 20 micrometers (0.00078 inches) and 100 micrometers (0.00394 inches). Each of the plurality of needles may be 70 micrometers (0.0027 inches) in diameter. The plurality of needles 105 includes four to six rows of needles spaced evenly apart on the outer surface 104 of the wheel 102, in some embodiments; the rows may be parallel circular rows evenly spaced on the outer surface of the wheel 102, where the wheel 102 is cylindrical. The needles 105 may have any shape conducive to piercing the stratum corneum of the user's skin. The needles may be substantially cylindrical with a sharpened tip. The needles may have the form of a pyramid. The needles may have the form of an obelisk. The needles may have the form of a substantially flat triangle. In some embodiments, each of the plurality of needles is substantially conical. In some embodiments, each needle has a cross-sectional area at the tip of the needle and a base where the needle joins the outer surface of the wheel, the base having a cross-sectional area at least eight times the cross-sectional area of the tip. The cross-sectional area may reduce from the base to the tip of the needle in any fashion as dictated by the shape of the needle. In some embodiments, the needles have heterogenous forms; for instance, some needles may be conical and others triangular or cylindrical. The base to tip width ratio of the needles may vary as well.

The device 100 may further include a reservoir 106 mounted on the head 101. The reservoir 106 may contain a fluid 107. The fluid 107 may be any material that behaves like a liquid when subjected to motive pressure as described in further detail below. The fluid 107 may be a liquid. The fluid 107 may be a gel. The fluid 107 may be a cream. The fluid 107 may be a lotion. The fluid 107 may be a viscoelastic substance that can be induced to behave in a fluid-like manner. The fluid 107 may be a non-Newtonian fluid. The fluid 107 may include one or more therapeutic agents; therapeutic agents may be any agents that have a potentially beneficial effect on the health or appearance of the user when applied using the device 100. The fluid 107 may contain agents including without limitation retinol (vitamin A), ascorbic acid (vitamin C), hyaluronic acid, or peptides. The fluid 107 may include cosmetic agents. The fluid 107 may include pharmaceutical agents. The reservoir 106 may have an opening 108 near to the wheel 102 such that the fluid 107 is disposed on the wheel 102 through the opening 108. In some embodiments, the reservoir 106 is contained in a tube 113 having a bottom end 114 near to the wheel 102 and a top end 115, wherein the opening 108 is in the bottom end 114 of the tube. The device 100 may further include a plunger 116 within the tube, and an actuator button 117 set through the top end of the tube and fixed to the plunger 116, such that depression of the actuator button 117 causes the plunger 116 to force the fluid 107 out through the opening 108. The space between the plunger 116 and the opening 108 may form the reservoir 106. The actuator button 117 may be connected to the plunger 116 via a rod 118; the rod may have a threaded portion that inserts into a reciprocally threaded cylindrical portion such that rotating the actuator button 117 also moves the plunger 116, allowing adjustments to ensure that depressing the actuator button 117 will always release a full amount of fluid 107. The tube 113 may be constructed from any material or combination of materials suitable for constructing the head 101.

In other embodiments, as shown in FIGS. 5A-B, the device 100 includes a mechanism 119 for automatically advancing the plunger each time the button 117 is depressed. FIG. 5A shows one embodiment of the mechanism 119 just after the actuator button (not shown) has been pressed. In this embodiment, the fluid 107 is contained in a tube and pushed toward one end of the tube using a plunger 116. Continuing the example, the plunger 116 is attached to a threaded rod 120 that is inserted in a reciprocally threaded hollow rod 121. In this example, the hollow rod 121 is fixed to a cam follower element 122 having a cam follower 123 that rests in a cylindrical cam 124 which revolves once around the interior of the tube. The top and bottom of the cam 124 are connected by a straight channel 125, in the example. In the example, pressing the button causes the plunger 116 to advance forward, forcing the fluid 107 through the opening, as the cam follower 123 travels down the straight channel. Continuing the example, as shown in FIG. 5B, upon the return stroke, a biasing means 126, such as a coiled compression spring, pushes the cam follower element 122 back toward the button, forcing the cam follower 123 to traverse the cylindrical cam 124, causing the hollow rod 121 to rotate with respect to the rod 120, which causes the rod 120 to extend further out of the hollow rod 121; a wedge cam set 127 may urge the cam follower element 122 toward the straight channel when the button is pressed, and toward the cylindrical cam 124 on the return stroke; alternatively, the cam 124 and straight shaft 125 may have angled portions at their ends that force the cam follower 123 into the cam 124 at the end of the pressing of the button and into the straight shaft 125 at the end of the return stroke. The cam follower 123 may also be shaped to engage the cam 124 during the return stroke and the shaft 125 during the pressing of the button. The threading of the rods 120, 121 may be calibrated so that the distance the rod 120 extends out of the hollow rod 121 is equivalent to the distance the plunger advances when the button 117 is pressed. Skilled practitioners in the art will be aware of variations to the above example that accomplish similar results. In other embodiments, the advancement of the plunger is achieved using a ratcheting process.

In some embodiments, device includes an airless pump situated to propel fluid through the opening. The airless pump may function by forming a vacuum near the opening 108 that draws fluid 107 through the opening, while allowing air to enter the top end 115 behind a plunger 116 that is drawn forward by the suction created when the fluid 107 is displaced. Persons skilled in the art will be aware of many designs for airless pumps that may be used as a component of the device 100. In other embodiments, as shown in FIG. 3A, the reservoir 106 is compressible to force the fluid 107 out through the opening 108. The reservoir 106 may be composed of a flexible, substantially inelastic material. The reservoir 106 may be composed of flexible plastic. The reservoir 106 may be composed of flexible metal, such as foil. The reservoir 106 may be composed of a flexible organic polymer. The reservoir 106 may be composed of a synthetic polymer. The reservoir 106 may be composed of a natural product such as leather. In some embodiments, the reservoir 106 is composed of a combination of two or more of the above-described materials. For instance, the reservoir 106 may be composed of metal foil and polymer. In some embodiments, the reservoir 106 is composed of a fibrous composite. The above-described methods for expelling fluid 107 from the reservoir 106 enable the device 100 to be used in any orientation without regard to gravity, allowing, for instance, the user to use the device on a vertical or overhanging skin surface. In some embodiments, the opening 108 further includes a nozzle.

Figure 6:
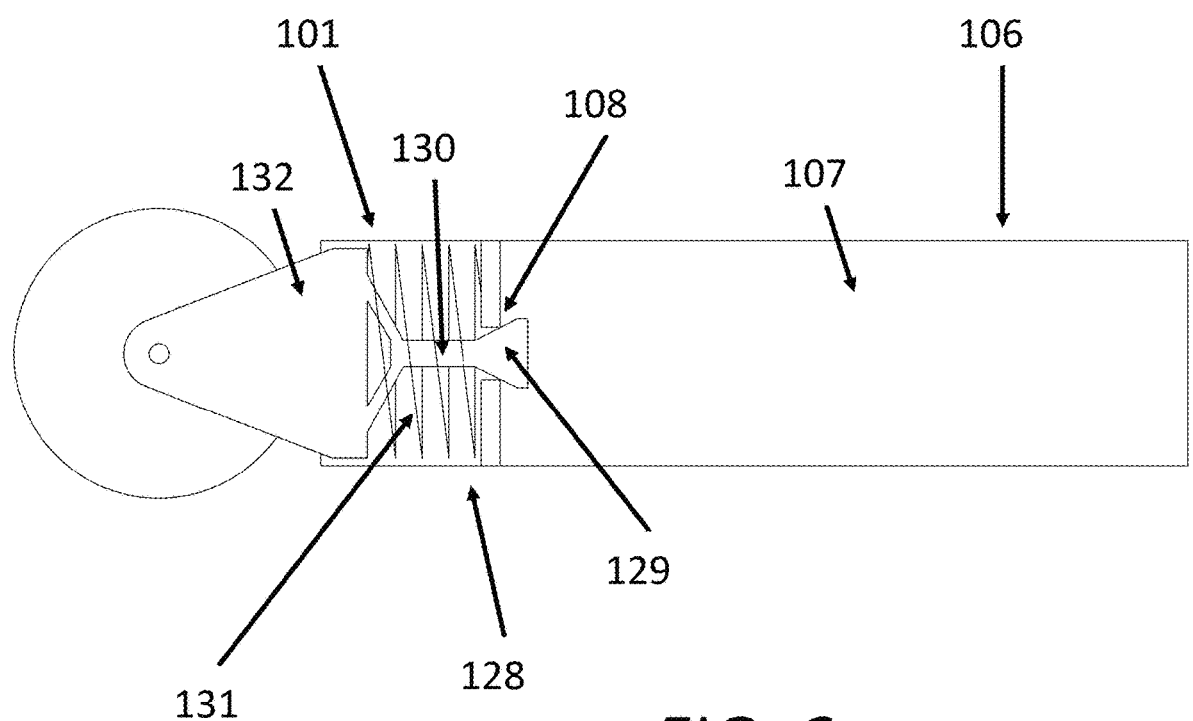
FIG. 6 is view of an embodiment of a valve in embodiments of the disclosed device.
Figure 8A:
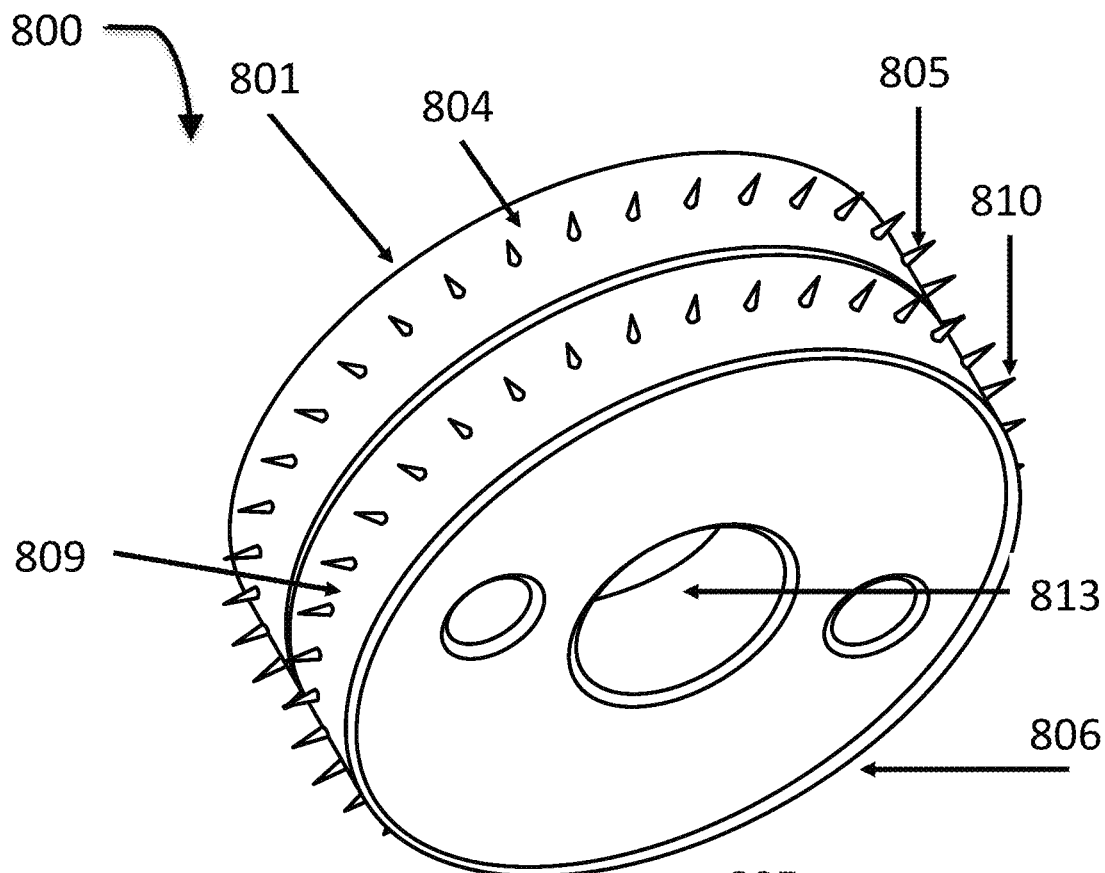
FIG. 8A is a schematic diagram of an embodiment of the device.
Figure 8B:
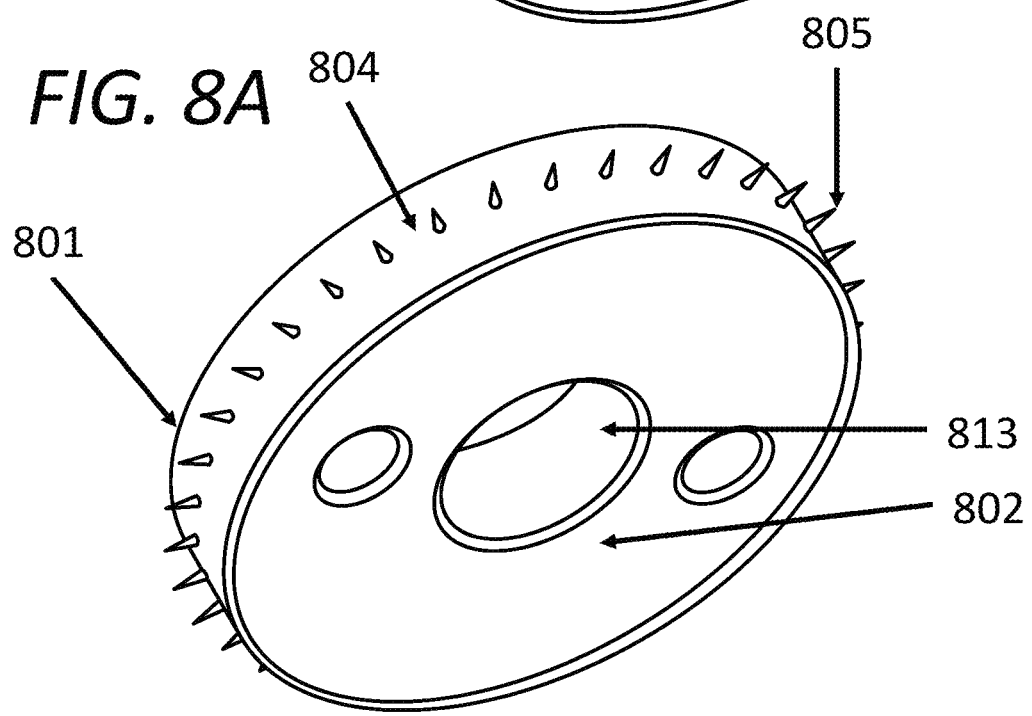
FIG. 8B is a schematic diagram of a wheel as described herein.
Figure 8C:
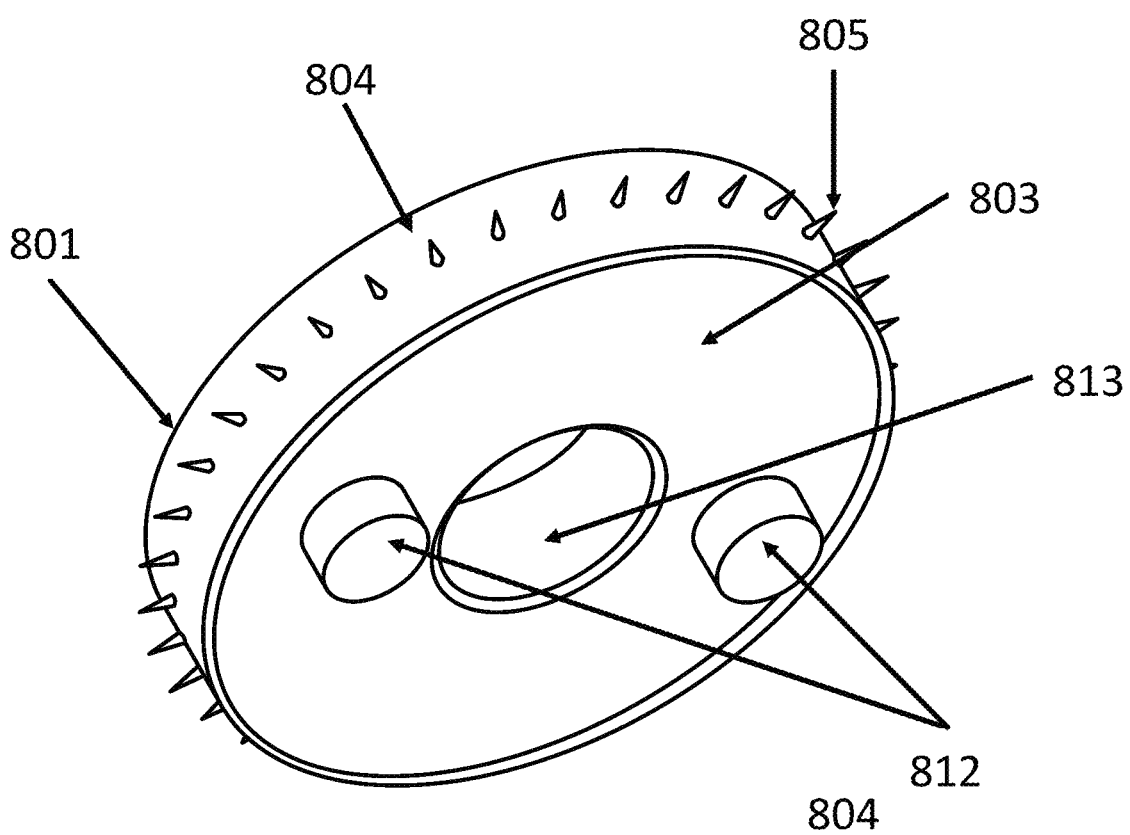
FIG. 8C is a schematic diagram of a wheel as described herein.
Figure 8D:
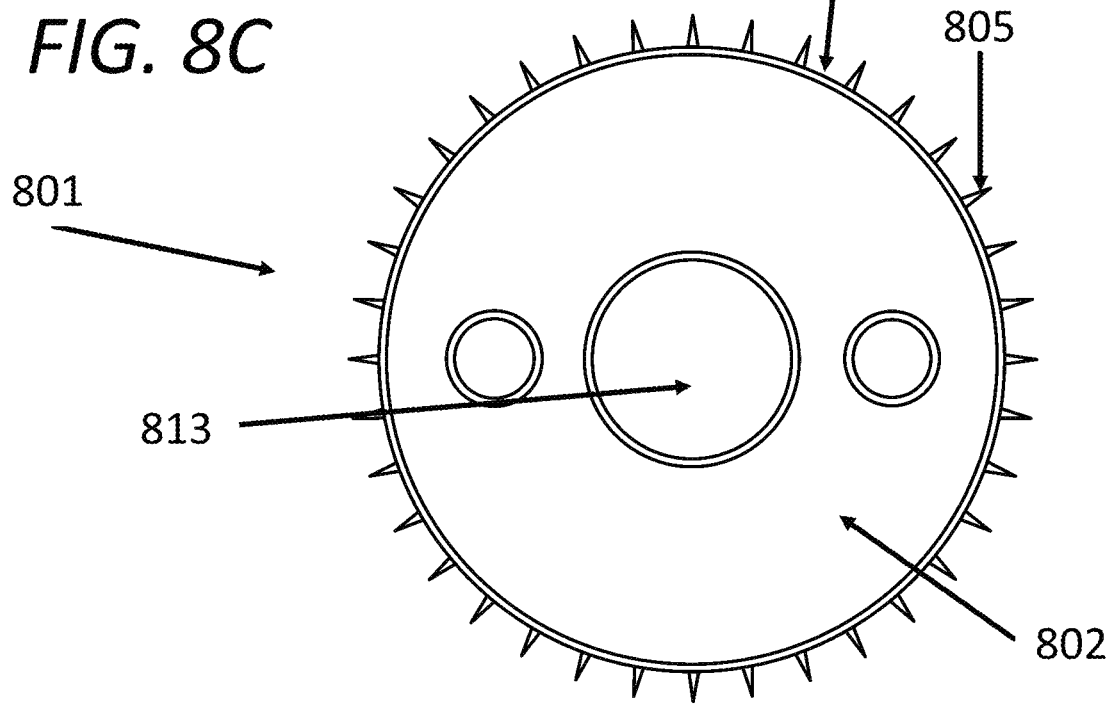
FIG. 8D is a schematic diagram of a wheel as described herein.
Figure 8E:
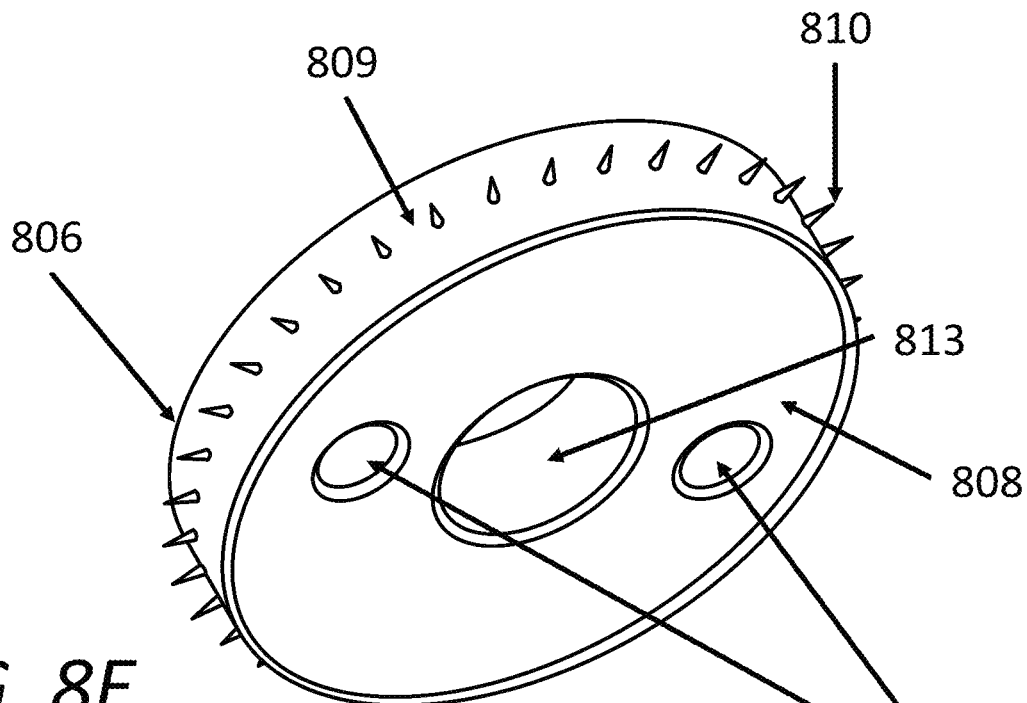
FIG. 8E is a schematic diagram of a wheel as described herein.
Figure 8F:
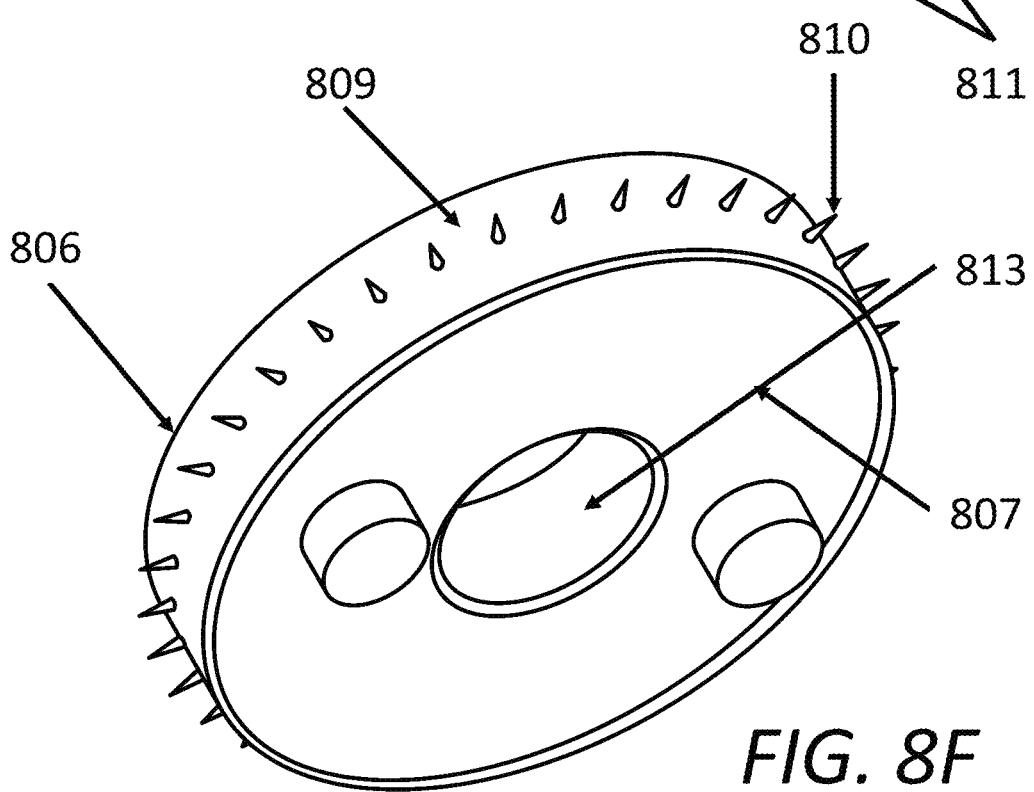
FIG. 8F is a schematic diagram of a wheel as described herein.

As shown in FIG. 6, the opening 108 may have a valve 128 that stops the opening 108 when the device 100 is not in use; the valve 128 may prevent the fluid 107 from passing through the opening 108 when the device 100 is not in use. In one embodiment, the valve 128 is a slit valve made up of a slit cut in elastic material; the elasticity of the material may exert a recoil force that holds the sides of the slit together so that the force that the fluid 107 exerts on the elastic material under the influence of gravity is insufficient to force the sides of the slit apart. The slit valve may deform during use to permit the fluid 107 to pass through it. The force exerted by the user to eject the fluid 107 from the reservoir 106 is sufficient to force the sides of the slit apart in some embodiments. The valve 128 may be a check valve. For instance, in another embodiment, the valve 128 includes a stopper inserted in the opening 108 from the direction of the head 101; the valve 128 in such an embodiment may include a biasing means such as a spring, whose bias urges the stopper into the opening with sufficient force to counteract the force exerted by the fluid 107 on the stopper under the influence of gravity. The bias of the biasing means may be such that the additional force exerted by the user to eject fluid 107 from the reservoir is sufficient to overcome the bias. Alternatively, in embodiments in which the user ejects the fluid 107 by means of an actuator button 117, the button 117 may also engage a member, such as a rod, that exerts a force on the stopper to push it out of the opening 108. In other embodiments, the valve 128 includes a stopper 129 inserted in the opening 108 from the direction of the reservoir 106, such that the force exerted by the fluid 107 on the stopper tends to push the stopper into the opening 108, sealing the opening 108 against leaks. In some embodiments, pressing the wheel against the user's skin causes a rod 130 to push the stopper out of the opening 108, allowing the fluid 107 to flow through the opening 108. In one embodiment, the head 101 is slideably movable with respect to the reservoir 106, and is fixedly attached to the rod such that pressure on the head causes the stopper to move out of the opening 108 and into the reservoir; a biasing means 131 such as a coiled compression spring may exert a recoil force urging the head away from the reservoir such that the stopper reinserts in the opening 108 when the pressure against the skin ceases. In another embodiment, the wheel 102 is slidably movable with respect to the head 101, and the rod is attached to the wheel 102 in a manner permitting the rod to transfer the motion of the wheel to the stopper without interfering with the rotation of the wheel; for instance, the wheel 102 may be journaled on a collar 132 that is fixed to the rod 130, the collar slideably movable with respect to the head 101. The collar may be set inside of the head 101 so that only pressure on the wheel 102 itself is likely to disengage the stopper; where there is a cap 135 as set forth below, the cap may cover the wheel and collar such that it is practically impossible to exert pressure on either the wheel or the collar without first removing the cap 135. The wheel 102 may be attached to the collar by any means by which the wheel is attachable to the head 101; the wheel 102 may be detachable from the collar in embodiments in which the wheel 102 may be detached and interchanged with other wheels. Some embodiments of the device also include a removable cap 135 that attaches to the head and covers the wheel.

FIG. 7 illustrates some embodiments of a method 700 for percutaneous delivery of therapeutic agents. The method 700 includes providing a device as described above in reference to FIGS. 1A-5 (701). The method 700 includes causing the fluid 107 to dispose from the opening 108 onto the wheel 102 (702). The method 700 includes rolling the wheel 102 firmly against skin of a user, causing the needles 105 to puncture the skin and deliver the fluid 107 into the punctures (703).

Referring to FIG. 7 in greater detail, and by reference to FIG. 1A-6, the method 700 includes providing a device as described above in reference to FIGS. 1A-6 (701). The device 100 may be previously assembled by a manufacturer. A user may assemble the device 100. The user may fill the reservoir 106 with the fluid 107. Where the head 101 is detachable, the user may attach the head 101 to the reservoir 106. The user may select the head 101 from a plurality of possible heads 101; for instance, where the skin to be treated is thick, the user may select a head 101 having millimeter-long (0.039 inch-long) microneedles instead of a head 101 having half-millimeter-long (0.002 inch-long) microneedles. Where the microneedles are constructed to dissolve upon insertion into skin, the user may select a head that includes microneedles containing the appropriate therapeutic substance. Likewise, where the wheel 102 is detachable from the head and interchangeable with other wheels, the user may select the appropriate wheel for the desired use. If the device 100 includes a cap 135, the user may remove the cap.

The method 700 includes causing the fluid 107 to dispose from the opening 108 onto the wheel 102 (702). In some embodiments, where the fluid 107 has low viscosity, the user may accomplish this by positioning the head downward, allowing gravity to carry the fluid 107 out the opening. Where there is a valve 128, the user may activate the valve to allow the fluid to flow; for instance, where the valve is activated by pressure against the wheel 102, the user may activate the valve upon placing the wheel on the skin. Where the reservoir 106 is contained in a tube 113 with a plunger 116 and actuator button 117, the user may cause the fluid 107 to dispose from the opening 108 onto the wheel 102 by depressing the actuator button as described above in reference to FIGS. 1A-2. Where the reservoir 106 is compressible, the user may cause the fluid 107 to dispose from the opening 108 by compressing the reservoir 106.

The method 700 includes rolling the wheel 102 firmly against skin of a user, causing the needles 105 to puncture the skin and deliver the fluid 107 into the punctures (703). The user may repeat the steps of causing the fluid 107 to dispose on the wheel 102 and rolling the wheel 102 on the skin one or more times, as needed to cover the region to be treated.

FIGS. 8A-F depict embodiments of a device 800 for percutaneous delivery of therapeutic agents. As a brief overview, the device 800 includes a first wheel 801. The first wheel 801 has a first axial surface 802. The first wheel 801 has a second axial surface 803. The first wheel 801 has an outer surface 804. The first wheel 801 includes plurality of needles 805 disposed upon the outer surface 804, each needle having a tip projecting away from the axis of rotation of the wheel. The device 800 includes a second wheel 806 having a first axial surface 807 affixed to the second axial surface 803 of the first wheel 801. The second wheel 806 has a second axial surface 808. The second wheel 806 has an outer surface 809, and a plurality of needles 810 disposed upon the outer surface 809, each needle having a tip projecting away from the axis of rotation.

Viewing FIGS. 8A-E in further detail, the device 800 includes a first wheel 801. The first wheel 801 may be composed of any material or combination of materials suitable for the construction of the wheel 102 described above. The first wheel 801 may have any suitable shape for a wheel; for instance, the first wheel 801 may be substantially cylindrical, toroidal, or a shape combining cylindrical and toroidal attributes, such as a cylinder with a rounded outer surface 804. In some embodiments, the outer surface 804 of the first wheel 801 is the surface that contacts a surface over which the first wheel 801 rolls; in other words, the outer surface 804 may serve the role of a rim, tread, or tire in a typical wheel. The plurality of needles 805 may be disposed on the outer surface 804 in any configuration suitable for the plurality of needles 105 described above. In some embodiments, the plurality of needles 805 is disposed in a substantially radially symmetrical array. The needles may be arranged in a single file forming a circle located halfway between the first axial surface 802 and the second axial surface 803 of the first wheel 801. Each of the plurality of needles 805 may have any form suitable for any of the plurality of needles 105 described above. Each of the plurality of needles 805 may be formed from any material or combination of materials suitable for forming the plurality of needles 105 described above.

The first wheel has a first axial surface 802. In some embodiments, the first axial surface 802 is substantially flat. In other embodiments, the first axial surface is curved or faceted. The first axial surface 802 may have any features that are suitable for the first axial surface 807 of the second wheel 806 as described in further detail below. The first axial surface 802 may have features that complement the features of the first axial surface 807 of the second wheel 806 as described in further detail below. The second axial surface 803 may have any form suitable for the first axial surface 802. In some embodiments, the second axial surface has substantially the same form as the second axial surface 808 of the second wheel 806, as described in further detail below.

The device 800 includes a second wheel 806 having a first axial surface 807 affixed to the second axial surface 803 of the first wheel 801. The second wheel 806 has a second axial surface 808. The second wheel 806 has an outer surface 809, and a plurality of needles 810 disposed upon the outer surface 809, each needle having a tip projecting away from the axis of rotation. The second wheel 806 may be made of any material or combination of materials suitable for the construction of the first wheel 801. The second wheel 806 may have any form suitable for the form of the first wheel 801.

The first axial surface 807 of the second wheel 806 is affixed to the second axial surface 803 of the first wheel 801. The two surfaces may be affixed together by any means, including adhesion, fastening with fasteners such as screws, rivets, or staples, attachment using heat such as soldering, welding, brazing, fusion bonding, or other means. In some embodiments, the first axial surface 807 of the second wheel 806 and the second axial surface 803 of the first wheel 801 have complementary features that affix the two surfaces together. For instance, in one embodiment, the first axial surface 807 of the second wheel 806 has at least one mortise 811, and second axial surface 803 of the first wheel 801 has at least one tenon 812 fitting in the at least one mortise 811. The at least one mortise 811 may be any depression in the first axial surface 807 of the second wheel 806, such as a cavity, hole, groove, slot, pit, or other feature, into which a projecting member on another object may be inserted. The at least one mortise 811 may have any shape; for instance, the mortise 811 may include a cylindrical or rectangular hole or pit, or a pit having any regular or irregular polygonal or curved cross-sectional form, as well as cross-sectional forms combining polygonal or curved elements. Likewise, the at least one mortise 811 may have any other form usable for a groove or other depression into which a projecting member may be fitted. The at least one tenon 812 may include a projecting member on the second axial surface 803 of the first wheel 801 that fits in the at least one mortice 811 to form a close and secure joint; the joint may be close and secure if the at least one tenon 812 exerts enough friction force on the at least one mortise 811, when inserted, to hold the second axial surface 803 of the first wheel 801 firmly against the first axial surface 807 of the second wheel. The shape of the at least one tenon 812 may be substantially the same as the shape of the mortise 811; for instance, the at least one mortise 811 may include a cylindrical cavity and the at least one tenon 812 may include a cylindrical projection having very slightly smaller dimensions than the at least one mortice 811, so that the at least one tenon 812 fits snugly within the at least one mortise 811. The at least one tenon 812 may have a shape that differs from the shape of the at least one mortise 811 while still fitting snugly within the at least one mortise 811; for instance, the mortise 811 may have a cylindrical shape and the tenon 812 may have a star-shaped or polygonal cross section, the vertices of which contact the side of the cylinder.

Figure 9:
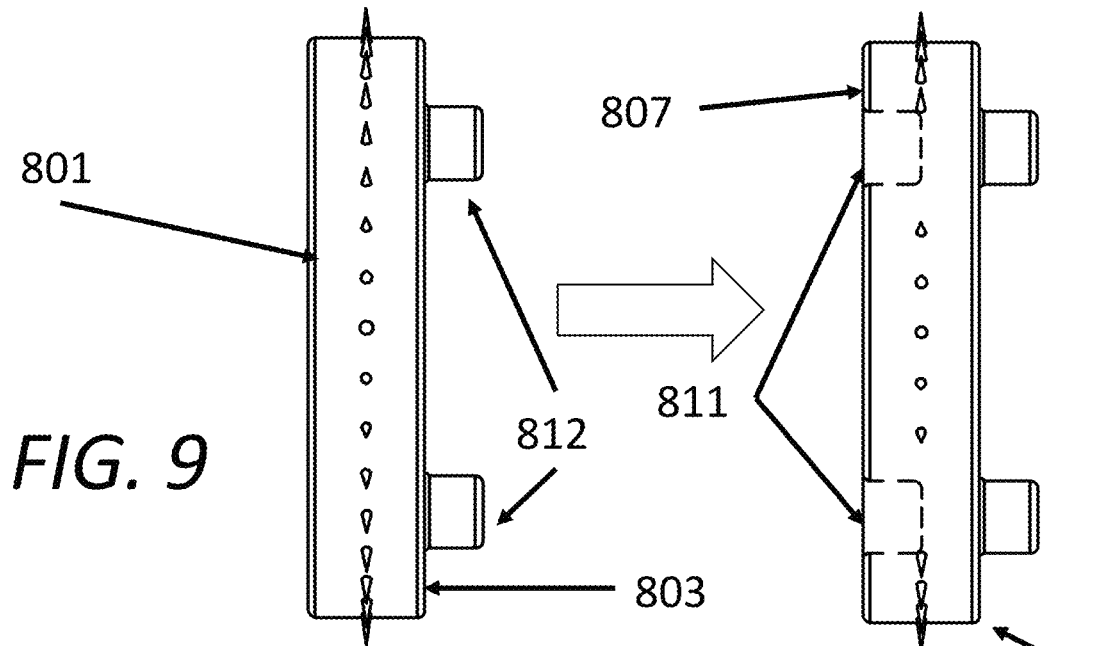
FIG. 9 is a schematic diagram of an embodiment of the device.

In some embodiments, there are two mortises in the second axial surface 803 of the first wheel 801 and there are two tenons on the first axial surface 807 of the second wheel 806. In other embodiments, at least one mortise is on the second axial surface 803 of the first wheel 801, and at least one tenon is on the second axial surface 803 of the first wheel 801, while a corresponding at least one tenon and at least one mortise may be found on the first axial surface 807 of the second wheel 806. As persons skilled in the art will be aware, the at least one mortise and at least one tenon may include more than two mortise and tenon combinations. The first wheel 801 and second wheel 806 may be joined by inserting the at least one tenon 812 into the at least one mortise 812, for instance as illustrated in FIG. 9.

In some embodiments, one or more features of the first wheel 801 are substantially identical to corresponding features of the second wheel 806. For instance, the first axial surface 802 of the first wheel 801 may be substantially the same as the first axial surface 807 of the second wheel 806. Likewise, the second axial surface 803 of the first wheel 801 may be substantially identical to the second axial surface 808 of the second wheel 806, or the outer surface 804 of the first wheel 801 may be substantially identical to the outer surface 809 of the second wheel 806. In some embodiments, the first wheel 801 is substantially identical to the second wheel 806; the first wheel 801 and second wheel 806 may be made using the same manufacturing process, for instance, in a plurality of substantially identical wheels are produced, and the first wheel 801 and second wheel 806 are two wheels of the plurality of substantially identical wheels.

Figure 10:
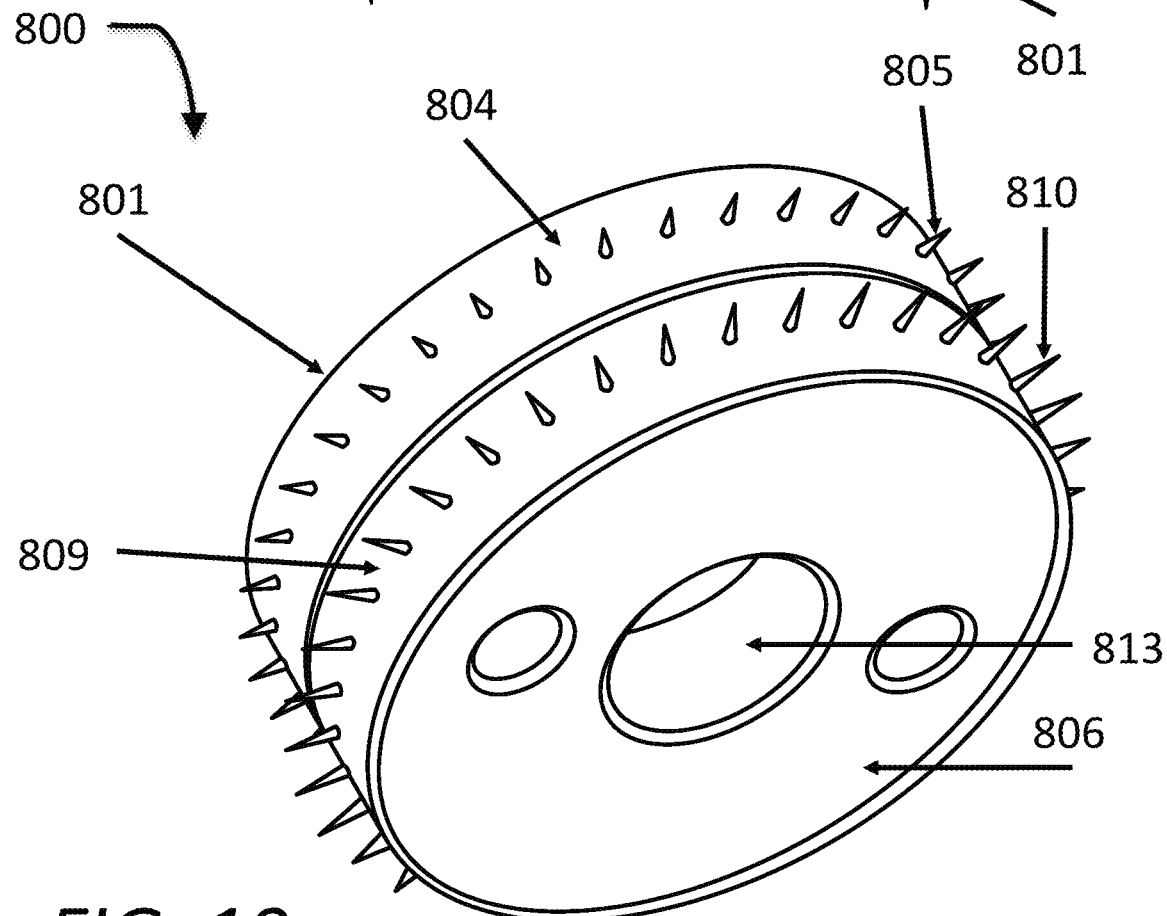
FIG. 10 is a schematic diagram of an embodiment of the device.

In some embodiments, as illustrated for instance in FIG. 10, each of the plurality of needles 805 mounted on the outer surface 804 of the first wheel 801 has a first length and each of the plurality of needles 810 mounted on the outer surface 809 of the second wheel 806 has a second length, the second length differing from the first length. The first length may be greater than the second length, or less than the second length. In some embodiments, this allows for the simple manufacturing process of a mesotherapy device having needles of varying lengths.

In some embodiments, as illustrated for example in FIG. 11, the device also includes a third wheel 1101 having an axis of rotation, a first axial surface 1102 affixed to the second axial surface of the second wheel 806, a second axial surface 1103, an outer surface 1104, and a plurality of needles 1105 disposed upon the outer surface 1104, each needle having a tip projecting away from the axis of rotation. The third wheel 1101 may have any form suitable for use as the first wheel 801 as described above. The third wheel 1101 may be constructed of any material or combination of materials suitable for the construction of the first wheel 801 as described above. The first axial surface 1102 of the third wheel 1101 may be attached to the second axial surface 808 of the second wheel 806 in any manner as described above, including joining using mortises and tenons. One or more features of the third wheel 1101 may be substantially identical to one or more features of the first wheel 801 or second wheel 806 as described above. The third wheel 1101 may be substantially identical to the first wheel 801 or the second wheel 806 as described above.

In some embodiments, each of the plurality of needles 805 mounted on the outer surface 804 of the first wheel 801 has a first length, each of the plurality of needles 810 mounted on the outer surface 809 of the second wheel 806 has a second length, and each of the plurality of needles 1105 mounted on the outer surface 1104 of the third wheel 1101 has a third length. As illustrated for example in FIG. 12, in some embodiments, the first length differs from the second length. In other embodiments, the first length differs from the third length. The second length may differ from the third length. As before, this enables the rapid manufacturing of a mesotherapy device having needles of up to three distinct lengths. In place of differing lengths, the needles may have different forms in other ways; for instance, the needles on the first wheel may have a different shape, thickness, or composition from the needles on the second wheel, which may have a different shape, thickness, or composition from the needles on the third wheel. Any manner of varying the needles as described above in reference to FIGS. 1A-6 may be used to vary the needles from one wheel to another wheel. Likewise, additional wheels (e.g., a fourth wheel, a fifth wheel, and so on) may be attached to the first, second, and third wheels.

Figure 13A:
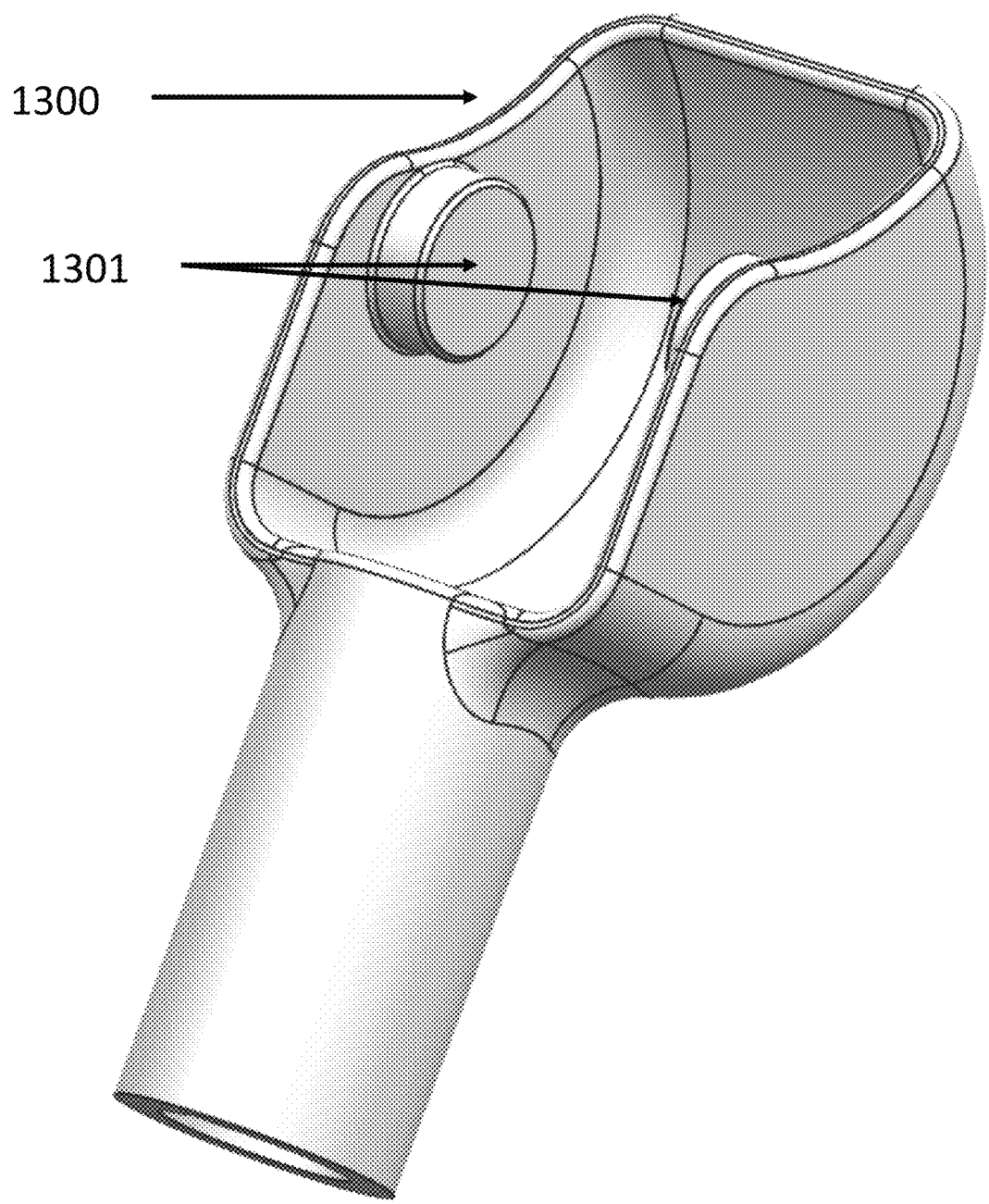
FIG. 13A is a schematic diagram of an embodiment of the device.
Figure 13B:
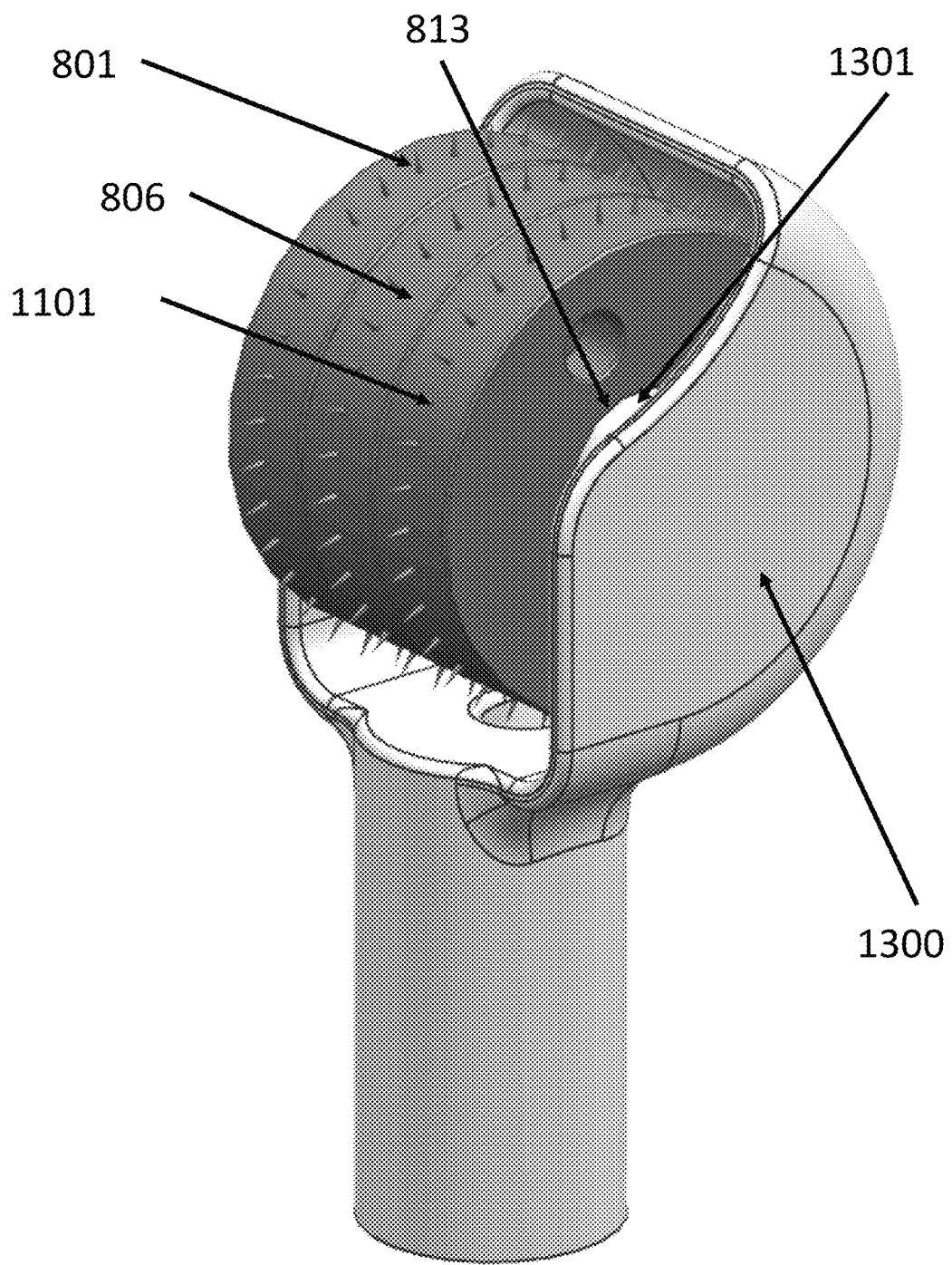
FIG. 13B is a schematic diagram of an embodiment of the device.

In some embodiments, as illustrated for example in FIGS. 13A-B, the mesotherapy device 800 has a head 1300. The head 1300 may be formed in any manner described above in reference to FIGS. 1A-6. The combined first wheel 801 and second wheel 806 may be journaled on the head in any manner disclosed above in reference to FIGS. 1A-6. For example, the third wheel may be rotably mounted on the head; the second or first axial surface of the third wheel may be rotably mounted on the head. Likewise, the first wheel may be rotably mounted on the head; the second or first axial surface of the first wheel may be rotably mounted on the head. Similarly, the second wheel may be rotably mounted on the head; the second or first axial surface of the second wheel may be rotably mounted on the head.

In some embodiments, as shown for instance in FIGS. 8A-F and 13B, the first wheel 801 and second wheel 806 have a central cavity 813; the central cavity 813 may be a hole through the first wheel 801 or second wheel 806 at the axis, or a pit in the first 802, 807 or second 803, 808 axial surfaces. In some embodiments, the central cavity 813 is radially symmetrical about the axis of rotation. The central cavity 813 may be circular; in other words, a cross-section taken of the central cavity in a plane perpendicular to the axis of rotation may have a circular perimeter. The central cavity 813 may be substantially cylindrical. In some embodiments, the head 1300 has at least one projection 1301 that fits in the central cavity 813. In some embodiments, a first projection 1301 on one side of the head fits into a central cavity 813 of the first wheel 801, and a second projection 1301 on the other side of the head 1300 fits into a central cavity 813 of another wheel, such as the second wheel or the third wheel.

The device 800 may include a reservoir mounted on the head, the reservoir containing a fluid, the reservoir having an opening near to the wheel such that the fluid is disposed on the wheel through the opening. This may be implemented as described above in reference to FIGS. 1A-6.

Figure 14:
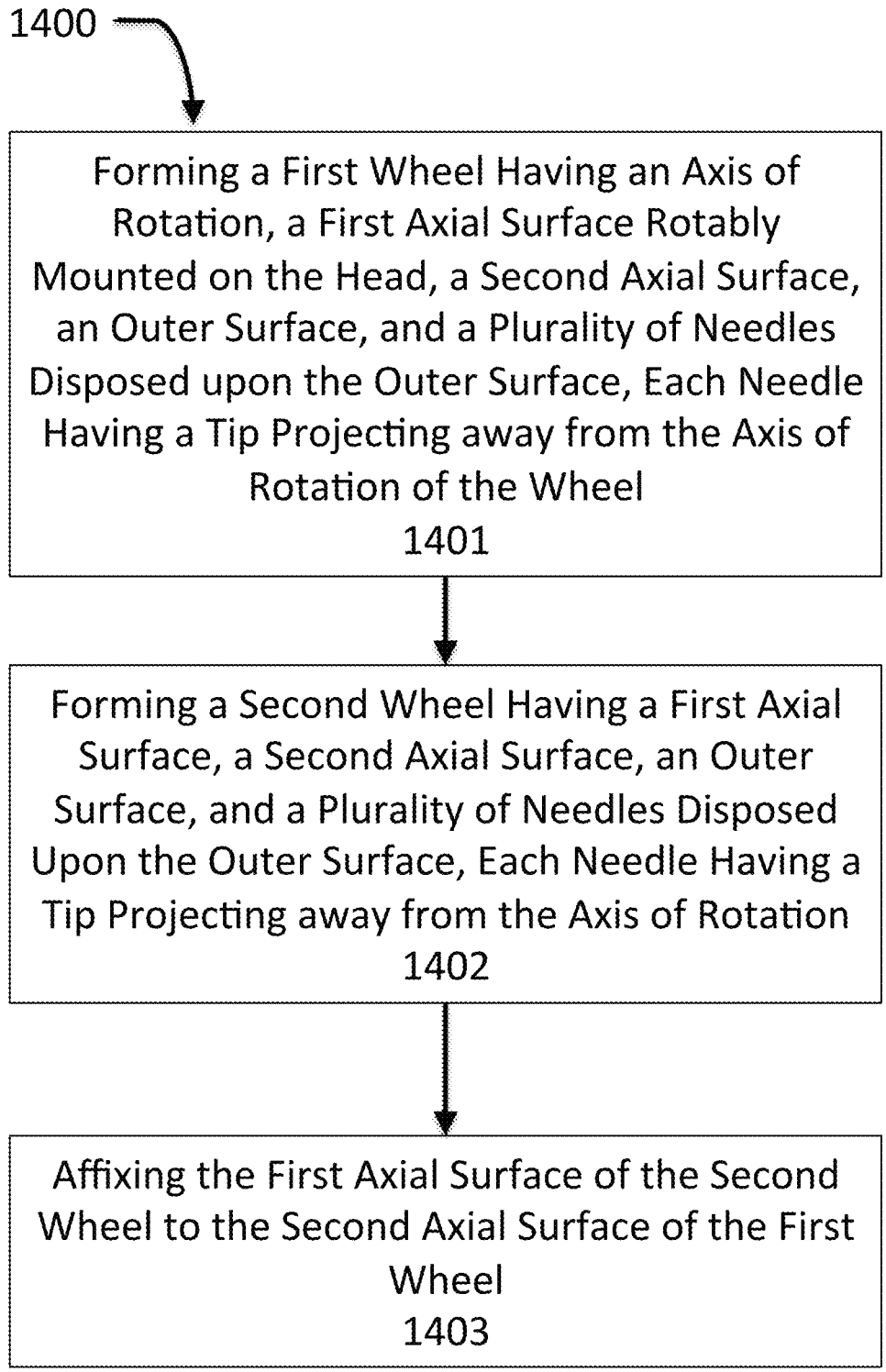
FIG. 14 is a flow chart illustrating one embodiment of the disclosed method.

FIG. 14 illustrates some embodiments of a method 1400 for manufacturing a device for percutaneous delivery of therapeutic agents. The method 1400 includes forming a first wheel having an axis of rotation, a first axial surface, a second axial surface, an outer surface, and a plurality of needles disposed upon the outer surface, each needle having a tip projecting away from the axis of rotation of the wheel (1401). The method 1400 includes forming a second wheel having a first axial surface, a second axial surface, an outer surface, and a plurality of needles disposed upon the outer surface, each needle having a tip projecting away from the axis of rotation (1402). The method 1400 includes affixing the first axial surface of the second wheel to the second axial surface of the first wheel (1403).

Referring to FIG. 14 in greater detail, and by reference to FIGS. 8A-13B, the method 1400 includes forming a first wheel having an axis of rotation, a first axial surface, a second axial surface, an outer surface, and a plurality of needles disposed upon the outer surface, each needle having a tip projecting away from the axis of rotation of the wheel (1401). The first wheel 801 may be formed by any process suitable for forming a rigid component, including but not limited to molding methods such as injection molding, extrusion, casting, stamping, rapid prototyping processes such as three-dimensional printing, thermoforming, machining, or any other fabrication methods. The first wheel 801 may be produced as a monolithic unit or by joining two or more pieces together to form the first wheel 801.

The method 1400 includes forming a second wheel having a first axial surface, a second axial surface, an outer surface, and a plurality of needles disposed upon the outer surface, each needle having a tip projecting away from the axis of rotation (1402). This may be implemented as described above for forming the first wheel 801.

The method 1400 includes affixing the first axial surface of the second wheel to the second axial surface of the first wheel (1403). This may be implemented as described above in reference to FIGS. 8A-13B. In some embodiments, where the first axial surface 807 of the second wheel 806 has at least one mortise 811, and the second axial surface 803 of the first wheel 801 has at least one tenon 812, affixing the second axial surface 803 of the first wheel 801 to the first axial surface 807 of the second wheel 806 further involves inserting or snapping the at least one tenon 812 into the at least one mortise 811.

It will be understood that the system and method may be embodied in other specific forms without departing from the spirit or central characteristics thereof. The present examples and embodiments, therefore, are to be considered in all respects as illustrative and not restrictive, and the device and method is not to be limited to the details given herein.

What is claimed is:

1. A device for percutaneous delivery of therapeutic agents, the device comprising:
   a head mounted on a body, said head comprising at least one projection;
   a first wheel having an axis of rotation, a first axial surface of the first wheel comprising a central cavity that engages with said projection such that the first axial surface of the first wheel is rotably mounted on the head, a second axial surface of the first wheel, an outer surface, and a plurality of needles disposed upon the outer surface, each needle having a tip projecting away from the axis of rotation of the wheel;
   a second wheel having an axis of rotation, a first axial surface of the second wheel coupled to the second axial surface of the first wheel, a second axial surface of the second wheel, an outer surface, and a plurality of needles disposed upon the outer surface, each needle having a tip projecting away from the axis of rotation;

a reservoir mounted on the body, wherein the reservoir is contained in a tube having a bottom end near to the wheel and a top end, wherein an opening is in the bottom end of the tube; and a plunger within the tube, and an actuator button set through the tip end of the tube and mechanically linked to the plunger, such that depression of the actuator button causes the plunger to force the fluid out through the opening.

2. The device of claim 1, wherein the opening further comprising a slit valve disposed across the opening that prevents the fluid from passing through the opening when the device is not in use.

3. The device of claim 1 wherein each of the plurality of needles mounted on the outer surface of the first wheel has a first length and each of the plurality of needles mounted on the outer surface of the second wheel has a second length, the second length differing from the first length.

4. The device of claim 1, wherein the first axial surface of the second wheel has at least one mortise, and the second axial surface of the first wheel has at least one tenon fitting in the at least one mortise.

5. The device of claim 1, further comprising a third wheel having an axis of rotation, a first axial surface of the third wheel affixed to the second axial surface of the second wheel, a second axial surface of the third wheel, an outer surface, and a plurality of needles disposed upon the outer surface, each needle having a tip projecting away from the axis of rotation.

6. The device of claim 5 wherein each of the plurality of needles mounted on the outer surface of the first wheel has a first length, each of the plurality of needles mounted on the outer surface of the second wheel has a second length, and each of the plurality of needles mounted on the outer surface of the third wheel has a third length.

7. The device of claim 6, wherein the first length differs from the second length.

8. The device of claim 6, wherein the first length differs from the third length.

9. The device of claim 6, wherein the second length differs from the third length.

10. The device of claim 6, wherein the third wheel has a central cavity on its second axial surface that engages with said projection on said head and is rotably mounted on the head.

11. The device of claim 1, wherein the second axial surface of the second wheel comprising a central cavity engages with said projection such that the second axial surface of the second wheel is rotably mounted on the head.

* * * * *